United States Patent
Verfaillie et al.

(10) Patent No.: US 8,426,200 B2
(45) Date of Patent: Apr. 23, 2013

(54) NEURONAL DIFFERENTIATION OF STEM CELLS

(75) Inventors: Catherine Verfaillie, St. Paul, MN (US); Yuehua Jiang, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 642 days.

(21) Appl. No.: 10/561,826

(22) PCT Filed: Jul. 2, 2004

(86) PCT No.: PCT/US2004/021553
§ 371 (c)(1),
(2), (4) Date: Oct. 17, 2006

(87) PCT Pub. No.: WO2005/003320
PCT Pub. Date: Jan. 13, 2005

(65) Prior Publication Data
US 2007/0059823 A1    Mar. 15, 2007

Related U.S. Application Data

(60) Provisional application No. 60/484,318, filed on Jul. 2, 2003.

(51) Int. Cl.
| | |
|---|---|
| C12N 5/071 | (2010.01) |
| C12N 5/0793 | (2010.01) |
| C12N 5/0797 | (2010.01) |
| C12N 5/0735 | (2010.01) |
| C12N 5/0789 | (2010.01) |
| C12N 5/077 | (2010.01) |
| C12N 5/0775 | (2010.01) |
| C12N 5/074 | (2010.01) |
| C12N 5/00 | (2006.01) |
| C12N 5/079 | (2010.01) |
| G01N 33/567 | (2006.01) |
| A01N 1/00 | (2006.01) |

(52) U.S. Cl.
USPC .......... 435/368; 435/326; 435/366; 435/7.21; 435/1.1; 435/384; 435/383; 435/391; 435/392; 435/389; 435/373

(58) Field of Classification Search .................. None
See application file for complete search history.

(56) References Cited

U.S. PATENT DOCUMENTS

| | | | |
|---|---|---|---|
| 5,589,376 A | 12/1996 | Anderson et al. | |
| 5,602,301 A | 2/1997 | Field | |
| 5,635,386 A | 6/1997 | Armstrong et al. | |
| 5,648,248 A | 7/1997 | Zenke et al. | |
| 5,654,183 A | 8/1997 | Anderson et al. | |
| 5,672,499 A | 9/1997 | Anderson et al. | |
| 5,733,727 A | 3/1998 | Field | |
| 5,851,832 A * | 12/1998 | Weiss et al. ................... | 435/368 |
| 5,906,934 A | 5/1999 | Grande et al. | |
| 5,928,943 A | 7/1999 | Franz et al. | |
| 6,015,671 A | 1/2000 | Field | |
| 6,214,369 B1 | 4/2001 | Grande et al. | |
| 6,284,539 B1 * | 9/2001 | Bowen et al. ................. | 435/455 |
| 6,306,575 B1 | 10/2001 | Thomas et al. | |
| 6,653,134 B2 | 11/2003 | Prockop et al. | |
| 6,777,231 B1 | 8/2004 | Katz et al. | |
| 7,015,037 B1 | 3/2006 | Furcht et al. | |
| 7,056,738 B2 | 6/2006 | Prockop et al. | |
| 7,129,034 B2 * | 10/2006 | Yu et al. ......................... | 435/1.1 |
| 7,229,827 B2 | 6/2007 | Kim et al. | |
| 2003/0003090 A1 | 1/2003 | Prockop et al. | |
| 2003/0059414 A1 | 3/2003 | Ho et al. | |
| 2003/0059939 A1 | 3/2003 | Page et al. | |
| 2003/0211605 A1 * | 11/2003 | Lee et al. ....................... | 435/368 |
| 2004/0235165 A1 | 11/2004 | Prockop et al. | |
| 2005/0169896 A1 | 8/2005 | Li et al. | |

FOREIGN PATENT DOCUMENTS

| | | |
|---|---|---|
| CA | 2191655 A | 6/1997 |
| EP | 0627487 A | 12/1994 |
| WO | WO 95/03062 | 2/1995 |
| WO | WO 95/10599 | 4/1995 |
| WO | WO 99/11758 | 3/1999 |
| WO | WO 99/35243 | 7/1999 |
| WO | WO 00/66713 | 11/2000 |
| WO | WO 01/51610 | 7/2001 |
| WO | WO 01/53461 | 7/2001 |
| WO | WO 01/68815 | 9/2001 |
| WO | WO 01/21766 | 3/2002 |
| WO | WO 02/086073 | 10/2002 |
| WO | WO02086073 | * 10/2002 |

OTHER PUBLICATIONS

Song et al. Methods in Mol. Biol. 2002. 198: 79-88.*
Walsh et al. (Neurosci. Lett 1992. 138: 103, abstract).*
Eglitis et al., "Hematopoietic cells differentiate into both microglia and macroglia in the brains of adult mice" Proc Nati Acad Sci USA; 94:4080-4085 (1997).
Kopen et al., "Marrow stromal cells migrate throughout forebrain and cerebellum, and they differentiate into astrocytes after injection into neonatal mouse brains" Proc Natl Acad Sci USA; 96:10711-10716 (1999).
Woodbury et al., "Adult rat and human bone marrow stromal cells differentiate into neurons" J. Neurosci. Res.; 61:364-370 (2000).
Bertani et al., "Neurogenic potential of human mesenchymal stem cells revisited: analysis by immunostaining, time-lapse video and microarray" J Cell Sci.; 118:3925-36 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype" J Neurosci Res; 77:192-204 (2004).
Jiang et al., "Pluripotency of mesenchymal stem cells derived from adult marrow, Supplemental Information for Verfaillie Corrigendum" Nature; 418:41-49 (2002).

(Continued)

Primary Examiner — Chang-Yu Wang
(74) Attorney, Agent, or Firm — Tarolli, Sundheim, Covell & Tummino LLP

(57) ABSTRACT

The present invention relates to compositions and methods for culturing stem cells, such that neuronal differentiation can be achieved.

4 Claims, 4 Drawing Sheets

OTHER PUBLICATIONS

Verfaillie, "Letter to the Editor" Experimental Hematology; (2007).
Aldous et al., "Flawed stem cell data withdrawn" New Scientist; (Feb. 15, 2007).
Aldous et al., "Fresh questions on stem cell findings" New Scientist; (Mar. 24, 2007).
Check "Stem cell paper corrected" Nature; 447:763 (2007) and Jiang et al., "Pluripotency of mesenchymal stem cells derived from adult bone marrow" Erratum in Nature; 447:879-880 (2007).
Chi, "Adult stem cell figure retracted" The Scientist; (Jun. 13, 2007).
Glenn, "Paper on versatility of adult stem cells comes under question" The Chronicle; (Feb. 26, 2007).
Holden, "Stem Cells. Controversial marrow cells coming into their own?" Science; 315:760-761 (2007).
Jiang et al., "Multipotent progenitor cells can be isolated from postnatal murine bone marrow, muscle, and brain" Exp. Hematol.; 30:896-904 (2002).
Lerner et al., "Stem cell study was flawed, U panel finds" Star Tribune; (Feb. 27, 2007).
Noonan, "Limitations on the usefulness of adult stem cells" Patent Docs; (Feb. 28, 2007).
Pincock, "Adult stem cell report questioned" The Scientist; (Feb. 26, 2007).
Reyes et al., "Purification and ex vivo expansion of postnatal human marrow mesodermal progenitor cells" Blood; 98:2615-25 (2001).
Serafini et al., "Hematopoietic reconstitution by multipotent adult progenitor cells: precursors to long-term hematopoietic stem cells" J. Exp. Med.; 204:129-39 (2007).
Brazelton et al., "From marrow to brain: expression of neuronal phenotypes in adult mice" Science; 290:1775-9 (2000).
Clarke et al., "Generalized potential of adult neural stem cells" Science, 288: 1660-3 (2000).
Johansson et al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).
Morshead et al., "Hematopoietic competence is a rare property of neural stem cells that may depend on genetic and epigenetic alterations" Nat. Med.; 8:268-73 (2002).
Sanchez-Ramos et al., "Adult bone marrow stromal cells differentiate into neural cells in vitro" Exp. Neurol.; 164:247-56 (2000).
Scintu et al., "Differentiation of human bone marrow stem cells into cells with a neural phenotype: diverse effects of two specific treatments" BMC Neurosci.; 7:14 (2006).
Prockop et al., "Marrow stromal cells are stem cells for nonhematopoietic tissues" Science; 276:71-74 (1997).
Chalmers-Redman et al., "In vitro propagation and inducible differentiation of mulipotential progenitor cells from human fetal brain" Neuroscience; 76:1121-1128 (1997).
Chen et al., "Therapeutic benefit of Intravenous administration of bone marrow stromal cells after cerebral ischemia in rats" Stroke; 32:1005-1011 (2001).
Reyes et al., "Turning marrow into brain: generation of glial and neuronal cells from adult bone marrow mesenchymal stem cells" Abstract 1676, American Society for Hematology (2001).
Gupta et al., "Human bone marrow derived mesodermal progenitor cells (MPC) in vitro correct the biochemical abnormality in Hurler Syndrome" Abstract 1199, American Society for Hematology (2001).
Reyes et al., "In vitro and in vivo characterization of neural cells derived from mesenchymal stem cells" Abstract 2126, American Society for Hematology (2001).
Zhao et al., "Immunohistochemical identification of multipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp Hematol; 30:896-904 (2002).
Zhao et al., "Human bone marrow stem cells exhibit neural phenotypes and ameliorate neurological deficits after grafting into the ischemic brain of rats" Exp Neurol; 174:11-20 (2002).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002) PMID: 12446433 [PubMed—in process].
Keene et al., "Phenotypic expression of transplanted human bone marrow-derived multipotent adult stem cells into the rat CNS" Exp. Neurology; 164:465 (2000).
Marmur et al., "Isolation and developmental characteristics of cerebral cortical multipotent progenitors" Developmental Biology; 204:577-591 (1998).
Sanchez-Ramos, J. "Neural cells derived from adult bone marrow and umbilical cord blood" J. Neuroscience Res; 69:880-893 (2002).
Giles, J., "The trouble with replication" Nature, 422:344-347 (2006).
Verfaillie, C.M., Multipotent adult progenitor cells: an update: Novartis Found. Symp., 254:55-65 (2005).

* cited by examiner

FIG. 4

Human Basic FGF (SEQ ID NO: 33)

1 mvgvgggdve dvlprpggcq lsgraargcn glpgaaawea alpmrpmh psvnprsraa
61 gsprtrgrrt eerpsgsrlg drgrgralpg grlggrgrgr apervggrgr grgtaapraa
121 paargsrpgp agtmaagsll tlpalpedgg sgafppghfk dpkrlyckng gfffrihpdg
181 rvdgvreksd phlkdqlqae ergvvslkgv canrylamke dgrllaskcv tdecfferl
241 esnnyntyrs rkytswyval krtgqyklgs ktgpgqkail flpmsaks

Human FGF-8 (SEQ ID NO: 34)

1 mgsprsalsc llhllvlcl qaqegpgrgp algrelaslf ragrepqgvs qqhvreqslv
61 tdqlsrrlir tyqlysrtsg khvqvlankr inamaedgdp faklivetdt fgsrvrvrga
121 etglyicmnk kgkliaksng kgkdcvftei vlennytalq nakyegwyma ftrkgrprkg
181 sktrqhqrev hfmkriprgh htteqslrfe flnyppftrs lrgsqrtwap epr isoform A (SEQ ID NO: 35)

1 mgsprsalsc llhllvlcl qaqhvreqsl vtdqlsrrl rtyqlysrts gkhvqvlank
61 rinamaedgd pfaklivetd tfgsrvrvrg aetglyicmn kkgkliaksn gkgkdcvfte
121 ivlennytal qnakyegwym aftrkgrprk gsktrqhqre vhfmkriprg hhtteqslrf
181 eflnyppftr slrgsqrtwa pepr isoform B (SEQ ID NO: 36)

1 mgsprsalsc llhllvlcl qaqvtvqssp nftqhvreqs lvtdqlsrrl lrtyqlysrt
61 sgkhvqvlan krinamaedg dpfaklivet dtfgsrvrvr gaetglyicm nkkgkliaks
121 ngkgkdcvft eivlennyta lqnakyegwy maftrkgrpr kgsktrqhqr evhfmkripr
181 ghhtteqslr feflnyppft rslrgsqrtw apepr isoform E (SEQ ID NO: 37)

1 mgsprsalsc llhllvlcl qaqegpgrgp algrelaslf ragrepqgvs qqhvreqslv
61 tdqlsrrlir tyqlysrtsg khvqvlankr inamaedgdp faklivetdt fgsrvrvrga
121 etglyicmnk kgkliaksng kgkdcvftei vlennytalq nakyegwyma ftrkgrprkg
181 sktrqhqrev hfmkriprgh htteqslrfe flnyppftrs lrgsqrtwap epr isoform F (SEQ ID NO: 38)

1 mgsprsalsc llhllvlcl qaqegpgrgp algrelaslf ragrepqgvs qqvtvqsspn
61 ftqhvreqsl vtdqlsrrl rtyqlysrts gkhvqvlank rinamaedgd pfaklivetd
121 tfgsrvrvrg aetglyicmn kkgkliaksn gkgkdcvfte ivlennytal qnakyegwym
181 aftrkgrprk gsktrqhqre vhfmkriprg hhtteqslrf eflnyppftr slrgsqrtwa
241 pepr

SEQUENCE LISTING

```
<160> NUMBER OF SEQ ID NOS: 40

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagatgcaca actcggagat cag                                              23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccatgaccta tactcaggct tcagg                                            25

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggcgctgtt cgcaaaga                                                    18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccaggcatca gagcacatca                                                  20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaacgcaaga gggatgaagg t                                                21
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtgtggcac ctggagttca                                               20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaggaaatgt accgtctgat gct                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgaagagagc ggagaaggag atc                                           23

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagaagacag tgaggcagat gagtta                                        26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggagtggt atcggtctaa gtttg                                         25

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgcagcttg ttcgactccg                                               20
```

-continued

```
<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aggttgaccg tgagagctga at                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcaatcatca ccacctccat ta                                              22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agttctccca ggacattgga ctt                                             23

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggatggagtc tgatgtcacc aa                                              22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttccaatgtg cagctgagtc                                                 20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtaatccgg gtgttccttc at                                              22

<210> SEQ ID NO 18
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaagctccat atccctgggt ggaaag                                          26

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cctcctcgcg catgaagat                                                  19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgtctgtgtg cctgacacat t                                               21

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aacaggtctc cccgcatct                                                  19

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caccctcagg aacagagtga ctt                                             23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcttgaccat catcttctcc agatc                                           25

<210> SEQ ID NO 24
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 24
tctggagtta agaaatcgga gctg                                              24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcctctgttc tccagcttgc t                                                 21

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccgctctag ggactcgtt                                                    19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgctctctg gctccttggc                                                   20

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgggcaggca tgggc                                                        15

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgggcacat tgtgcttctg                                                   20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 30
acacagccca aactccacag t					21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgacgtttct caggcattaa gc					22

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggtgcacttg cttgtgcagt					20

<210> SEQ ID NO 33
<211> LENGTH: 288
<212> TYPE: PRT
<213> ORGANISM: Homo sapiens
<220> FEATURE:
<223> OTHER INFORMATION: Human Basic FGF
<220> FEATURE:
<223> OTHER INFORMATION: Cytokine

<400> SEQUENCE: 33

Met Val Gly Val Gly Gly Gly Asp Val Glu Asp Val Thr Pro Arg Pro
1               5                   10                  15

Gly Gly Cys Gln Ile Ser Gly Arg Ala Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

```
Ile Lys Leu Gln Leu Gln Ala Glu Glu Arg Gly Val Ser Ile Lys
        195                 200                 205

Gly Val Cys Ala Asn Arg Tyr Leu Ala Met Lys Glu Asp Gly Arg Leu
210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
                275                 280                 285

<210> SEQ ID NO 34
<211> LENGTH: 233
<212> TYPE: PRT
<213> ORGANISM: Homo sapiens
<220> FEATURE:
<223> OTHER INFORMATION: Human FGF-8
<220> FEATURE:
<223> OTHER INFORMATION: Cytokine

<400> SEQUENCE: 34

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Arg Gly Pro Ala Leu
                20                  25                  30

Gly Arg Glu Leu Ala Ser Leu Phe Arg Ala Gly Arg Gly Pro Gln Gly
            35                  40                  45

Val Ser Gln Gln His Val Arg Glu Gln Ser Leu Val Thr Asp Gln Leu
        50                  55                  60

Ser Arg Arg Leu Ile Arg Thr Tyr Gln Leu Tyr Ser Arg Thr Ser Gly
65                  70                  75                  80

Lys His Val Gln Val Leu Ala Asn Lys Arg Ile Asn Ala Met Ala Glu
                85                  90                  95

Asp Gly Asp Pro Phe Ala Lys Leu Ile Val Glu Thr Asp Thr Phe Gly
                100                 105                 110

Ser Arg Val Arg Val Arg Gly Ala Glu Thr Gly Leu Tyr Ile Cys Met
                115                 120                 125

Asn Lys Lys Gly Lys Leu Ile Ala Lys Ser Asn Gly Lys Gly Lys Asp
130                 135                 140

Cys Val Phe Thr Glu Ile Val Leu Glu Asn Asn Tyr Thr Ala Leu Gln
145                 150                 155                 160

Asn Ala Lys Tyr Glu Gly Trp Tyr Met Ala Phe Thr Arg Lys Gly Arg
                165                 170                 175

Pro Arg Lys Gly Ser Lys Thr Arg Gln His Gln Arg Glu Val His Phe
                180                 185                 190

Met Lys Arg Leu Pro Arg Gly His His Thr Thr Glu Gln Ser Leu Arg
            195                 200                 205

Phe Glu Phe Leu Asn Tyr Pro Pro Phe Thr Arg Ser Leu Arg Gly Ser
        210                 215                 220

Gln Arg Thr Trp Ala Pro Glu Pro Arg
225                 230

<210> SEQ ID NO 35
<211> LENGTH: 204
<212> TYPE: PRT
<213> ORGANISM: Homo sapiens
```

```
<220> FEATURE:
<223> OTHER INFORMATION: Isoform A
<220> FEATURE:
<223> OTHER INFORMATION: Cytokine

<400> SEQUENCE: 35

Met Gly Ser Pro Arg Ser Ala Leu Ser Cys Leu Leu Leu His Leu Leu
1               5                   10                  15

Val Leu Cys Leu Gln Ala Gln His Val Arg Glu Gln Ser Leu Val Thr
            20                  25                  30

Asp Gln Leu Ser Arg Arg Leu Ile Arg Thr Tyr Gln Leu Tyr Ser Arg
        35                  40                  45

Thr Ser Gly Lys His Val Gln Val Leu Ala Asn Lys Arg Ile Asn Ala
    50                  55                  60

Met Ala Glu Asp Gly Asp Pro Phe Ala Lys Leu Ile Val Glu Thr Asp
65                  70                  75                  80

Thr Phe Gly Ser Arg Val Arg Val Arg Gly Ala Glu Thr Gly Leu Tyr
                85                  90                  95

Ile Cys Met Asn Lys Lys Gly Lys Leu Ile Ala Lys Ser Asn Gly Lys
            100                 105                 110

Gly Lys Asp Cys Val Phe Thr Glu Ile Val Leu Glu Asn Asn Tyr Thr
        115                 120                 125

Ala Leu Gln Asn Ala Lys Tyr Glu Gly Trp Tyr Met Ala Phe Thr Arg
    130                 135                 140

Lys Gly Arg Pro Arg Lys Gly Ser Lys Thr Arg Gln His Gln Arg Glu
145                 150                 155                 160

Val His Phe Met Lys Arg Leu Pro Arg Gly His His Thr Thr Glu Gln
                165                 170                 175

Ser Leu Arg Phe Glu Phe Leu Asn Tyr Pro Pro Phe Thr Arg Ser Leu
            180                 185                 190

Arg Gly Ser Gln Arg Thr Trp Ala Pro Glu Pro Arg
        195                 200

<210> SEQ ID NO 36
<211> LENGTH: 215
<212> TYPE: PRT
<213> ORGANISM: Homo sapiens
<220> FEATURE:
<223> OTHER INFORMATION: Isoform B
<220> FEATURE:
<223> OTHER INFORMATION: Cytokine

<400> SEQUENCE: 36

Met Gly Ser Pro Arg Ser Ala Leu Ser Cys Leu Leu Leu His Leu Leu
1               5                   10                  15

Val Leu Cys Leu Gln Ala Gln Val Thr Val Gln Ser Ser Pro Asn Phe
            20                  25                  30

Thr Gln His Val Arg Glu Gln Ser Leu Val Thr Asp Gln Leu Ser Arg
        35                  40                  45

Arg Leu Ile Arg Thr Tyr Gln Leu Tyr Ser Arg Thr Ser Gly Lys His
    50                  55                  60

Val Gln Val Leu Ala Asn Lys Arg Ile Asn Ala Met Ala Glu Asp Gly
65                  70                  75                  80

Asp Pro Phe Ala Lys Leu Ile Val Glu Thr Asp Thr Phe Gly Ser Arg
                85                  90                  95

Val Arg Val Arg Gly Ala Glu Thr Gly Leu Tyr Ile Cys Met Asn Lys
            100                 105                 110

Lys Gly Lys Leu Ile Ala Lys Ser Asn Gly Lys Gly Lys Asp Cys Val
```

```
            115                 120                 125
Phe Thr Glu Ile Val Leu Glu Asn Asn Tyr Thr Ala Leu Gln Asn Ala
    130                 135                 140

Lys Tyr Glu Gly Trp Tyr Met Ala Phe Thr Arg Lys Gly Arg Pro Arg
145                 150                 155                 160

Lys Gly Ser Lys Thr Arg Gln His Gln Arg Glu Val His Phe Met Lys
                165                 170                 175

Arg Leu Pro Arg Gly His His Thr Thr Glu Gln Ser Leu Arg Phe Glu
            180                 185                 190

Phe Leu Asn Tyr Pro Pro Phe Thr Arg Ser Leu Arg Gly Ser Gln Arg
        195                 200                 205

Thr Trp Ala Pro Glu Pro Arg
    210                 215

<210> SEQ ID NO 37
<211> LENGTH: 234
<212> TYPE: PRT
<213> ORGANISM: Homo sapiens
<220> FEATURE:
<223> OTHER INFORMATION: Isoform E
<220> FEATURE:
<223> OTHER INFORMATION: Cytokine

<400> SEQUENCE: 37

Met Gly Ser Pro Arg Ser Ala Leu Ser Cys Leu Leu His Leu Leu
1               5                   10                  15

Val Leu Cys Leu Gln Ala Gln Glu Gly Pro Gly Arg Gly Pro Ala Leu
            20                  25                  30

Glu Gly Arg Glu Leu Ala Ser Leu Phe Arg Ala Gly Arg Glu Pro Gln
        35                  40                  45

Gly Val Ser Gln Gln His Val Arg Glu Gln Ser Leu Val Thr Asp Gln
    50                  55                  60

Leu Ser Arg Arg Leu Ile Arg Thr Tyr Gln Leu Tyr Ser Arg Thr Ser
65                  70                  75                  80

Gly Lys His Val Gln Val Leu Ala Asn Lys Arg Ile Asn Ala Met Ala
                85                  90                  95

Glu Asp Gly Asp Pro Phe Ala Lys Leu Ile Val Glu Thr Asp Thr Phe
            100                 105                 110

Gly Ser Arg Val Arg Val Arg Gly Ala Glu Thr Gly Leu Tyr Ile Cys
        115                 120                 125

Met Asn Lys Lys Gly Lys Leu Ile Ala Lys Ser Asn Gly Lys Gly Lys
    130                 135                 140

Asp Cys Val Phe Thr Glu Ile Val Leu Glu Asn Asn Tyr Thr Ala Leu
145                 150                 155                 160

Gln Asn Ala Lys Tyr Glu Gly Trp Tyr Met Ala Phe Thr Arg Lys Gly
                165                 170                 175

Arg Pro Arg Lys Gly Ser Lys Thr Arg Gln His Gln Arg Glu Val His
            180                 185                 190

Phe Met Lys Arg Leu Pro Arg Gly His His Thr Thr Glu Gln Ser Leu
        195                 200                 205

Arg Phe Glu Phe Leu Asn Tyr Pro Pro Phe Thr Arg Ser Leu Arg Gly
    210                 215                 220

Ser Gln Arg Thr Trp Ala Pro Glu Pro Arg
225                 230

<210> SEQ ID NO 38
<211> LENGTH: 244
```

```
<212> TYPE: PRT
<213> ORGANISM: Homo sapiens
<220> FEATURE:
<223> OTHER INFORMATION: Isoform F
<220> FEATURE:
<223> OTHER INFORMATION: Cytokine

<400> SEQUENCE: 38

Met Gly Ser Pro Arg Ser Ala Leu Ser Cys Leu Leu Leu His Leu Leu
1               5                   10                  15

Val Leu Cys Leu Gln Ala Gln Glu Gly Pro Gly Arg Gly Pro Ala Leu
            20                  25                  30

Gly Arg Glu Leu Ala Ser Leu Phe Arg Ala Gly Arg Glu Pro Gln Gly
        35                  40                  45

Val Ser Gln Gln Val Thr Val Gln Ser Ser Pro Asn Phe Thr Gln His
    50                  55                  60

Val Arg Glu Gln Ser Leu Val Thr Asp Gln Leu Ser Arg Arg Leu Ile
65                  70                  75                  80

Arg Thr Tyr Gln Leu Tyr Ser Arg Thr Ser Gly Lys His Val Gln Val
                85                  90                  95

Leu Ala Asn Lys Arg Ile Asn Ala Met Ala Glu Asp Gly Asp Pro Phe
            100                 105                 110

Ala Lys Leu Ile Val Glu Thr Asp Thr Phe Gly Ser Arg Val Arg Val
        115                 120                 125

Arg Gly Ala Glu Thr Gly Leu Tyr Ile Cys Met Asn Lys Lys Gly Lys
    130                 135                 140

Leu Ile Ala Lys Ser Asn Gly Lys Gly Lys Asp Cys Val Phe Thr Glu
145                 150                 155                 160

Ile Val Leu Glu Asn Asn Tyr Thr Ala Leu Gln Asn Ala Lys Tyr Glu
                165                 170                 175

Gly Trp Tyr Met Ala Phe Thr Arg Lys Gly Arg Pro Arg Lys Gly Ser
            180                 185                 190

Lys Thr Arg Gln His Gln Arg Glu Val His Phe Met Lys Arg Leu Pro
        195                 200                 205

Arg Gly His His Thr Thr Glu Gln Ser Leu Arg Phe Glu Phe Leu Asn
    210                 215                 220

Tyr Pro Pro Phe Thr Arg Ser Leu Arg Gly Ser Gln Arg Thr Trp Ala
225                 230                 235                 240

Pro Glu Pro Arg

<210> SEQ ID NO 39
<211> LENGTH: 462
<212> TYPE: PRT
<213> ORGANISM: Homo sapiens
<220> FEATURE:
<223> OTHER INFORMATION: Human Sonic Hedgehog

<400> SEQUENCE: 39

Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80
```

```
Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Ser Leu His Tyr Glu Gly Arg
    130                 135                 140

Ala Val Asp Ile Thr Thr Ser Asp Arg Asp Ser Lys Tyr Gly Met
145                 150                 155                 160

Leu Ala Arg Leu Ala Val Glu Ala Gly Phe Asp Trp Val Tyr Tyr Glu
            165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
            195                 200                 205

Gln Gly Gly Thr Lys Leu Val Lys Asp Leu Ser Pro Gly Asp Arg Val
            210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
            290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
            355                 360                 365

Glu His Ser Trp Ala His Arg Ala Phe Ala Pro Phe Arg Leu Ala His
            370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
            435                 440                 445

Ser Glu Ala Leu His Pro Leu Gly Met Ala Val Lys Ser Ser
            450                 455                 460

<210> SEQ ID NO 40
<211> LENGTH: 247
<212> TYPE: PRT
<213> ORGANISM: Homo sapiens
<220> FEATURE:
<223> OTHER INFORMATION: Human brain-derived neurotrophic factor
```

```
<400> SEQUENCE: 40

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
        50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
        210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245
```

NEURONAL DIFFERENTIATION OF STEM CELLS

RELATED APPLICATIONS/PATENTS & INCORPORATION BY REFERENCE

This application claims priority to U.S. Application Ser. No. 60/484,318, filed Jul. 2, 2003.

STATEMENT OF RIGHTS TO INVENTIONS MADE UNDER FEDERALLY SPONSORED RESEARCH

This work was supported by NIH Grants RO1-DK061847, RO1-DK58295. The government may have certain rights to the invention.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself, and, each of these documents or references ("herein-cited references"), as well as each document or reference cited in each of the herein-cited references (including any manufacturer's specifications, instructions, etc.), is hereby expressly incorporated herein by reference. Reference is specifically made to PCT application Nos. PCT/US01/02064748, filed on Aug. 4, 2000 (published as WO 01/110011 on Feb. 15, 2001), and PCT/US02/04652 filed on Feb. 14, 2002 (published as WO 02/064748 on Aug. 22, 2002), the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 26, 2013, is named 89003-2006.1_SL.txt and is 26,582 bytes in size.

FIELD OF THE INVENTION

The present invention relates to compositions and methods for culturing stem cells (e.g., multipotent adult progenitor cells, or "MAPCs"), such that neuronal differentiation is achieved. Other aspects of the invention are described in or are obvious from the following disclosure, and are within the ambit of the invention.

BACKGROUND OF THE INVENTION

Stem cells are capable of forming at least one, and sometimes many, specialized cell types. Non-embryonic stem cells include, for example, neural stem cells, hematopoietic stem cells, endothelial progenitor cells, and mesenchymal stem cells. Until recently, it was thought that such cells were progenitor cells that could only differentiate into cell lineages derived from the tissue of origin (i.e., that hematopoietic stem cell could only differentiate into hematopoietic lineages). However, several recent studies indicate that these cells can differentiate into cells of different lineages (Ferrari, G. et al, 1998; Gussoni, E. et al, 1999; Rafli, S. et al, 1994; Asahara, T. et al, 1997; Lin, Y. et al, 2000; Orlic, D. et al, 2001; Jackson, K. et al, 2001; Petersen, B. E. et al, 1999; Theise, N. D. et al, 2000; Lagasse, E. et al, 2000; Petersen, B. E. et al, 1999; Theise, N. D. et al, 2000; Lagasse, E. et al, 2000; Krause, D. S. et al, 2001; Mezey, E. et al, 2000; Brazelton, T. R. et al, 2000; Orlic, D. et al, 2001; Bjornson, C. et al, 1999; Shih, C. C. et al, 2001; Jackson, K. et al, 1999; Kawada, H. and Ogawa, M., 2001). Multipotent adult progenitor cells, or MAPCs, for example, home to liver, lung, gut and bone marrow and spleen when transfused into murine recipients, where they differentiate in a tissue specific manner.

Despite recent advances in selection techniques, simple, efficient and highly effective culture conditions for use in the differentiation of stem cells into several terminally differentiated cell types have yet to be developed. Neuronal cells are an example of a cell type for which improved methods of differentiation methods are needed. A number of studies have found that terminal neuronal differentiation requires yet-to-be characterized factors secreted by region-specific glial cells. For instance, Wagner et al found that co-culture of Nurr1 neurons with type-II astrocytes from primary E16 rat ventral mesencephalon, the age and region where endogenous neurons of the substantia nigra have just been born, yielded a significant numbers of functioning dopaminergic neurons (Wagner, J. et al, 1999). Panchision et al created a type-II astrocyte line that supports terminal differentiation of dopaminergic neurons (Panchision, D. M. et al, 1999). Song et al also demonstrated that neural differentiation in vitro occurred when NSCs were co-cultured with brain-derived astrocytes (Song, H. et al, 2002). With the exception of perhaps neuronal stem cells, culture conditions for stem cells have not been shown to consistently produce neuronal cells that have undergone developmentally correct progression throughout the in vitro differentiation process (i.e., show morphological and biochemical changes that temporally correspond to those seen in vivo differentiation).

Obtaining neuronal cells suitable for transplantation will have great use in the treatment of neurodegenerative diseases, such as amyotrophic lateral sclerosis, Alzheimer's, and Parkinson's disease. Stem cells, such as MAPCs, can potentially serve as an unlimited source of neuronal tissue for such purposes. Accordingly, culture conditions that achieve differentiation of stem cells to functional neuronal cells that mimics in vivo differentiation would be desirable.

SUMMARY OF THE INVENTION

The present invention relates to methods of culturing stem cells, such that neuronal differentiation can be achieved.

In one aspect, the present invention relates to methods for inducing stem cells to differentiate into neuronal cells comprising sequentially providing specific factors to stem cells in culture. The methods produce cells having undergone biochemical and morphological changes that are characteristic of developing neuronal cells in vivo.

Neuronal cells produced by methods of the present invention have a mature phenotype and display neuronal function. Neuronal cells produced by methods of the present invention include, but are not limited to, dopaminergic, serotonergic and GABA-ergic neurons.

In one embodiment, the present invention relates to a method for inducing stem cells to differentiate into neuronal cells, said method comprising the steps of:
a) culturing stem cells with basic fibroblast growth factor;
b) culturing the cells of step a) with fibroblast growth factor 8 and Sonic Hedgehog;

c) culturing the cells of step b) with brain-derived neurotrophic factor; and d) co-culturing the cells of step c) with astrocytes.

In one exemplified embodiment, astrocytes are derived from fetal brain.

In one embodiment, co-culturing is in a medium having a supplement comprising insulin, transferrin, selenite, putrescine and progesterone.

In an exemplified embodiment, the co-culturing is in a medium containing N2 SUPPLEMENT®.

At each successive step, culturing is for about 5 to 15 days, most preferably for at least 7 days.

Stem cells include, but are not limited to, embryonic stem cells and adult stem cells, such as multipotent adult progenitor cells (MAPCs).

In one embodiment, the stem cells are maintained in the presence of fibronectin.

Other aspects of the invention are described in or are obvious from the following disclosure, and are within the ambit of the invention.

BRIEF DESCRIPTION OF THE FIGURES

FIG. 4 depicts the amino acid sequences of basic fibroblast growth factor, fibroblast growth factor 8, Sonic Hedgehog (SEQ ID NO: 39), and brain-derived neurotrophic factor (SEQ ID NO: 40).

DETAILED DESCRIPTION OF THE INVENTION

Figure 1:
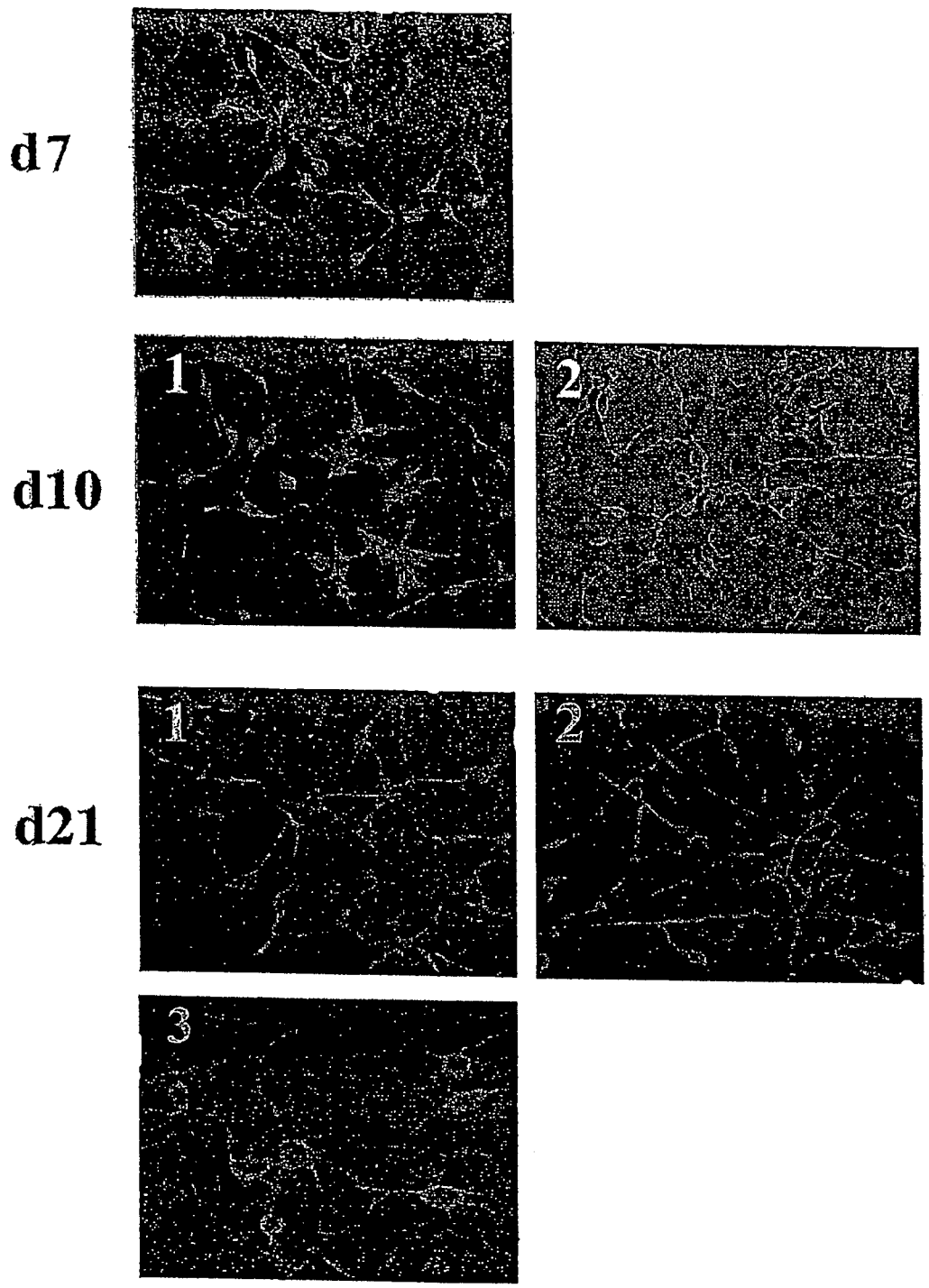
FIG. 1 shows mouse MAPCs that were cultured sequentially for 7 days with 100 ng/mL bFGF, 10 ng/mL FGF8 and 10 ng/mL SHH, and 10 ng/mL BDNF on fibronectin coated chamber slides. After 7, 10 and 21 days, cells were fixed and stained with antibodies against D7: nestin and Nurr1, followed by secondary Cy5 and Cy3 coupled antibodies respectively; D10: (1) NF200 and GFAP, followed by secondary Cy3 and Cy5 coupled antibodies respectively; and (2) NF200 and MBP, followed by secondary Cy3 and Cy5 coupled antibodies respectively; D21: (1) GABA and DDC, followed by secondary Cy5 and Cy3 coupled antibodies respectively; (2) TrH and TH, followed by secondary Cy5 and Cy3 coupled antibodies respectively; and (3) MAP2AB and Tau, followed by secondary Cy3 and Cy5 coupled antibodies respectively.

As used herein, the terms below are defined by the following meanings:

"Stem cell" refers to a cell that can give rise to at least two cell types of the ectodermal lineage. A "MAPC" is one type of stem cell. Another is an "embryonic stem cell."

"MAPC" is an acronym for a multipotent adult progenitor cell. It refers to a non-embryonic stem cell that can give rise to cell lineages of all three germ layers upon differentiation. See PCT/US00/21387, published as WO 01/11011, and filed as U.S. application Ser. No. 10/048,757 (specifically incorporated by reference for the description of MAPC isolation, characterization and preparation) and PCT/US02/04652, published as WO 02/064748, and filed as U.S. application Ser. No. 10/467,963 (specifically incorporated by reference for the description of MAPC isolation, characterization and preparation).

"Germ layers" are the three primary layers formed as a result of gastrulation in early stage embryos, consisting of endoderm, mesoderm and ectoderm. Embryonic germ layers are the source from which all tissues and organs derive. The endoderm is the source of, for example, pharynx, esophagus, stomach, intestine and associated glands (e.g., salivary glands), liver, epithelial linings of respiratory passages and gastrointestinal tract, pancreas and lungs. The mesoderm is the source of, for example, smooth and striated muscle, connective tissue, vessels, the cardiovascular system, blood cells, bone marrow, skeleton, reproductive organs and excretory organs. Ectoderm is the source of, for example, epidermis (epidermal layer of the skin), sensory organs, the entire nervous system, including brain, spinal cord, and all the outlying components of the nervous system.

"Multipotent" refers to the ability to give rise to more than one differentiated cell type. MAPCs have extensive multipotency, in that they can give rise to cell lineages of all three germ layers (i.e., endoderm, mesoderm and ectoderm) upon differentiation.

"Progenitor cells" are cells produced during differentiation of a stem cell and have some, but not all, of the characteristics of their terminally differentiated progeny. Defined progenitor cells are committed to a lineage, but not to a specific or terminally differentiated cell type. The term "progenitor" as used in the acronym "MAPC" does not limit these cells to a particular lineage.

"Neuronal differentiation factors" are chemical or biological factors that induce differentiation of stem cells into cells of the neuronal lineage. Neuronal differentiation factors of the invention include, but are not limited to, basic fibroblast growth factor, fibroblast growth factor-8, brain-derived neurotrophic factor, Sonic Hedgehog, N2 SUPPLEMENT®, and combinations thereof that are capable of modulating neuronal differentiation of stem cells in culture.

The terms "comprises", "comprising", and the like can have the meaning ascribed to them in U.S. Patent Law and can mean "includes", "including" and the like.

Methods and Compositions of the Invention

Methods of the present invention induce stem cells in culture to progresses through the appropriate stages of neuronal development, thus recapitulating neuronal development in vitro, and as a result, give rise to cells having functional neuronal properties (e.g., biochemical, anatomical, and electrophysiological characteristics of midbrain neuronal cells).

Culture methods of the invention comprise an ordered addition of neuronal differentiation factors, wherein there is a first addition of basic fibroblast growth factor (Abraham, J. A., 1986); a second addition of fibroblast growth factor 8 (Gemel, J., 1996; Yoshiura, K., 1997) and Sonic Hedgehog (Marigo, V., 1995); a third addition of brain-derived neurotrophic factor (Maisonpierre, P. C., 1991) followed by co-culture with fetal brain astrocytes. Co-culturing can be performed in a medium having a supplement comprising insulin, transferrin, selenite, putrescine and progesterone. In an exemplified embodiment, the co-culturing is in a medium containing N2 SUPPLEMENT®, available from Gibco (Catalog No. 17502048, containing recombinant human insulin, human transferrin (iron-saturated), sodium selenite, putrescine and progesterone in Phosphate Buffered Saline).

Additional components can be added as necessary at each step. For example, PDGF and/or EGF may be present together with bFGF. Similarly, inhibitors of WNT and TGF-β/BMPs (e.g., Noggin) may be present together with bFGF.

At each successive step, the culture is continued for about 5 to 15 days, most preferably for at least 7 days. Optionally, each sequential step comprises only the specified growth factor(s). Medium can be Prepared to contain only the growth factor(s) of interest, and cells can be washed between steps to reduce the presence of previously added growth factor(s). Alternatively, reduced concentrations of the previously provided factor remain in the culture medium.

The amounts of each neuronal differentiation factor can vary, for example, depending on the stem cell selected and the size and duration of the culture. Concentrations can range, for example, between 10-20 ng/mL, 20-30 ng/mL, 30-40 ng/mL, 40-50 ng/mL, 50-60 ng/mL, 60-70 ng/mL, 70-80 ng/mL, 80-90 ng/mL and 90-100 ng/mL. In a specific embodiment, 100 ng/mL bFGF, 10 ng/mL FGF-8, 100 ng/mL SHH and 10 ng/mL BDNF are used. Suitable concentrations can be determined by assaying the differentiation potential of stem cells having undergone the sequential culture methods of the invention.

The neuronal differentiation factors of the present invention are well known in the art. Human basic fibroblast growth factor is described by at least Abraham et al., 1986, the contents of which are incorporated herein by reference. Sequence information for human basic fibroblast growth factor is available as Genbank Accession No. NP_001997 (FIG. 4).

Human fibroblast growth factor 8 is described by at least Gemel et al, 1996 and Yoshiura et al, 1997, the contents of which are incorporated herein by reference. Sequence information for human fibroblast growth factor 8 is available as Genbank Accession Nos. P55075, NP_149355, NP_006110, NP_149353, and NP_149354. (FIG. 4).

Human Sonic Hedgehog is described by at least Marigo et al, 1995, the contents of which are incorporated herein by reference. Sequence information for human sonic hedgehog is available as Genbank Accession No. Q15465 (FIG. 4).

Human brain-derived neurotrophic factor is described by at least Maisonpierre et al, 1991, the contents of which are incorporated herein by reference. Sequence information for human brain-derived neurotrophic factor is available as Genbank Accession No. P23560 (FIG. 4).

Methods of the invention contemplate the use of any basic fibroblast growth factor, fibroblast growth factor 8, Sonic Hedgehog, or brain-derived neurotrophic factor known in the art and having conserved function, and from all species (e.g., orthologues from human, mouse, rat, monkey, pig and the like).

Suitable forms of basic fibroblast growth factor, fibroblast growth factor 8, Sonic Hedgehog, or brain-derived neurotrophic factor can comprise isolated polypeptides, that are optionally recombinant, including whole proteins, partial proteins (e.g., domains) and peptide fragments. Fragments of a polypeptide preferably are those fragments that retain the distinct functional capability of the particular factor, which in this case generally relates the ability to influence neuronal differentiation (the specific function of each factor is well known in the art). Such polypeptides can also comprise, for example, fusion proteins and chimeric proteins. Short polypeptides can be synthesized chemically using well-established methods of peptide synthesis.

The invention also contemplates the use variants of neuronal differentiation factors described above (i.e., basic fibroblast growth factor, fibroblast growth factor 8, Sonic Hedgehog, or brain-derived neurotrophic factor). As used herein, a "variant" of a polypeptide is a polypeptide which contains one or more modifications to the primary amino acid sequence. Variants would include allelic variants and polymorphic variants having conserved function. Modifications which create a polypeptide variant can also be made to 1) enhance a property of a polypeptide, such as protein stability in an expression system or the stability of protein-protein binding; or 2) to provide a novel activity or property to a polypeptide, such as addition of a detectable moiety. Modifications to a polypeptide can be introduced by way of the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence.

The skilled artisan will also realize that conservative amino acid substitutions may be made in the neuronal differentiation factors described above to provide functionally equivalent variants of the foregoing polypeptides, i.e., the variants retaining functional capabilities. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York.

Conservative amino-acid substitutions in amino acid sequences typically are made by alteration of the coding nucleic acid encoding. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488492, 1985), or by chemical synthesis of a coding gene. Where amino acid substitutions are made to a small peptide fragment, the substitutions can be made by directly synthesizing the peptide. The activity of functionally equivalent fragments of polypeptides can be tested by cloning the gene encoding the altered polypeptide into a bacterial or mammalian expression vector, introducing the vector into an appropriate host cell, expressing the altered polypeptide, and testing for a functional capability. Peptides which are chemically synthesized can be tested directly for function.

Stem cell lines and other fastidious cells benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce. Where neuronal differentiation is desired, stem cells of the invention can benefit from co-culturing with glioma, neuroblastoma, oligodendrocyte, microglial, and astrocyte cell-types. Cells available for co-culturing with stem cells are often inactivated by γ-irradiation, similar to feeder cell layers. One embodiment of the present invention uses astrocytes, such as brain-derived astrocytes in co-culture with stem cells. Astrocytes can be obtained from any suitable (or species compatible) source of brain, including fetal or adult brain.

Stem cells can be maintained and allowed to expand in culture medium (i.e., an "initial culture") that is well established in the art and commercially available from the American Type Culture Collection (ATCC). Such media include, but are not limited to, DULBECCO'S MODIFIED EAGLE'S MEDIUM® (DMEM), DMEM F12 MEDIUM®, EAGLE'S MINIMUM ESSENTIAL MEDIUM®, F-12K MEDIUM®, ISOCOVE'S MODIFIED DULBECCO'S MEDIUM®, RPMI-1640 MEDIUM®. It is within the skill of one in the art to modify or modulate concentrations of media and media supplements as necessary for the stem cells used. It will also be apparent that many media are available as a low-glucose formulation, with or without sodium pyruvate.

Where it is desired for the stem cells to remain in an undifferentiated state, the medium can contain supplements such as epidermal growth factor (EGF), platelet derived growth factor (PDGF), leukemia inhibitory factor (LIF), and combinations thereof. It is apparent to those skilled in the art that supplements that allow the cell to self-renew but not differentiate can be removed from the culture medium prior to differentiation.

In an embodiment specific for MAPCs, supplements are cellular factors or components that allow MAPCs to retain the ability to differentiate into all three lineages. This may be indicated by the expression of specific markers of the undifferentiated state. MAPCs, for example, constitutively express Oct 3/4 (Oct 3A) and maintain high levels of telomerase.

Assays for monitoring gene expression are well known in the art (e.g., RT-PCR), and can be conducted using standard methodology.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade.

Additional supplements can also be used to supply the stem cells with the necessary trace elements for optimal growth and expansion. Such supplements include insulin, transferrin, sodium selePillm and combinations thereof. These components can be included in a salt solution such as, but not limited to HANK'S BALANCED SALT SOLUTION® (HESS), EARLE'S SALT SOLUTION®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (FUNGIZONE®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin. Antibiotic and anti-mycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be used in cell culture and include, but are not limited to D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. One embodiment uses linoleic acid conjugated to albumin.

Also contemplated is the use of feeder cell layers. Feeder cells are used to support the growth of fastidious cultured cells, including stem cells. Feeder cells are normal cells that have been inactivated by γ-irradiation. In culture, the feeder layer serves as a basal layer for other cells and supplies important cellular factors without further growth or division of their own. Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability, and expansion of stem cells. In many cases, feeder cell layers are not necessary to keep the stem cells in an undifferentiated, proliferative state, as leukemia inhibitory factor (LIF) has anti-differentiation properties. Often, supplementation of a defined concentration of LIF is all that is necessary to maintain stem cells in an undifferentiated state.

Cells in culture can be maintained either in suspension or attached to a solid support, such as extracellular matrix components. Stem cells often require additional factors that encourage their attachment to a solid support, such as type I and type II collagen, chondroitin sulfate, fibronectin, "super-fibronectin", and fibronectin-like polymers, gelatin, poly-D and poly-L-lysine, thrombospondin, and vitronectin. One embodiment utilizes fibronectin.

Neuronal cells produced by methods of the present invention have a mature phenotype and display neuronal function. Monitoring the progress of neuronal differentiation can involve, for example, screening for expression of genetic markers of neuronal differentiation. Developmental progression of the cells in culture can be monitored, for example, by measuring levels of neuroectodermal transcripts including, but not limited to, mRNA for c-Ret, sox1, otx2, otx1, pax2, pax5, and Nurr1, nestin, GFAP, MBP, NF200, Dopamine, TH, GABA, TrH, and DBH. Assays for monitoring gene expression are well known in the art (e.g., RT-PCR), and can be conducted using standard methodology.

Methods of identifying and subsequently separating differentiated cells from their undifferentiated counterparts can be carried out by methods well known in the art. Cells that have been induced to differentiate using methods of the present invention can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e. formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and enzyme-linked immunosorbent assay (ELISA). From the standpoint of transcriptional upregulation of specific genes, differentiated cells often display levels of gene expression that are different from undifferentiated cells. Reverse-transcription polymerase chain reaction, or RT-PCR, can also be used to monitor changes in gene expression in response to differentiation. Whole genome analysis using microarray technology can also be used to identify differentiated cells. In the case of neural cells, patch-clamp electrophysiology is another method by which differentiated cells can be advantageously identified.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. One embodiment of the invention envisions the use of FACS to identify and separate cells based on cell-surface antigen expression.

Compositions and methods of the present invention can result in neuronal cell lines or neuronal cell populations suitable for administration into a mammalian host. The neuronal cell population can be engrafted into specific locations of the central and peripheral nervous system (preferably brain or spinal cord), such that the function of a cell or organ, defective due to injury, genetic disease, acquired disease or iatrogenic treatments, is augmented, reconstituted or even provided for the first time.

Stem Cells of the Present Invention

In general, stem cells of the present invention comprise those having the capacity for neuronal differentiation.

In one embodiment, the stem cells are MAPCs (Jiang, Y. et al, 2002). MAPCs derived from human, mouse, rat or other mammals appear to be the only normal, non-malignant, somatic cell (i.e., non-germ cell) known to date to express very high levels of telomerase even in late passage cells. The telomeres are extended in MAPCs and they are karyotypically normal. Because MAPCs injected into a mammal can migrate to and assimilate within multiple organs, MAPCs are self-renewing stem cells. As such, they have utility in the repopulation of organs, either in a self-renewing state or in a differentiated state compatible with the organ of interest. They have the capacity to replace cell types that could have been damaged, died, or otherwise might have an abnormal function because of genetic or acquired disease.

Human MAPCs are described in U.S. application Ser. No. 10/048,757 (see page 8, lines 23-32; p. 9, lines 1-22; p. 21, lines 19-32; p. 22, lines 1-27; p. 25, lines 20-31; pages 26 through p. 28, lines 1-13, 20-25; p. 29, lines 1-21) and U.S. application Ser. No. 10/467,963 (see p. 9, lines 29-32; p. 10, lines 1-25), specifically incorporated by reference for the characterization of MAPCs.

Methods of MAPC isolation are described in U.S. application Ser. No. 10/048,757 (p. 10, lines 17-32; p. 11, lines 1-12; p. 22, lines 29-32; p. 23, lines 1-32; p. 24, lines 1-28; p. 71, lines 28-32; p. 72 through p. 74, lines 1-27) and U.S. application Ser. No. 10/467,963 (p. 26, lines 13-34; p. 27 through p. 28, lines 1-27), specifically incorporated by reference for the methods of isolation described. Methods of MAPC culture are also described in U.S. application Ser. No. 10/048, 757 (p. 23, lines 25-32) and U.S. application Ser. No. 10/467, 963 (p. 26, lines 18-29), specifically incorporated by reference for the culture methods described.

Stem cells used in the present invention can also include embryonic stem cells (Lebkowski, J. S. et al, 2001). The quintessential stem cell is the embryonic stem (ES) cell, as it has unlimited self-renewal and pluripotent differentiation potential (Thomson, J. et al. 1995; Thomson, J. A. et al. 1998; Shamblott, M. et al. 1998; Williams, R. L. et al. 1988; Orkin, S. 1998; Reubinoff, B. E., et al. 2000). These cells are derived from the inner cell mass (ICM) of the pre-implantation blastocyst (Thomson, J. et al. 1995; Thomson, J. A. et al. 1998; Martin, G. R. 1981), or can be derived from the primordial germ cells from a post-implantation embryo (embryonal germ cells or EG cells). ES and/or EG cells have been derived from multiple species, including mouse, rat, rabbit, sheep, goat, pig and, more recently, from human and non-human primates (U.S. Pat. Nos. 5,843,780 and 6,200,806).

Stem cells of the present invention also include those known in the art that have been identified in organs or tissues (non-embryonic stem cells), such as neural stem cells (NSCs) (Gage F. H. 2000; Svendsen C. N. et al, 1999; Okabe S. et al. 1996). Several studies in rodents, and more recently, non-human primates and humans, have shown that stem cells persist in adult brain. These stem cells can proliferate in vivo and continuously regenerate at least some neuronal cells in vivo. When cultured ex vivo, NSCs can be induced to proliferate, as well as to differentiate into different types of neurons and glial cells. When transplanted into the brain, NSCs can engraft and generate neural cells and glial cells.

NSCs have been identified in the sub-ventricular zone (SVZ) and the hippocampus of the adult mammalian brain (Ciccolini et al., 1998; Morrison et al., 1999; Palmer et al., 1997; Reynolds and Weiss, 1992; Vescovi et al., 1999) and can also be present in the ependyma and other presumed non-neurogenic areas of the brain (Doetsch et al., 1999; Johansson et al., 1999; Palmer et al., 1999). Fetal or adult brain-derived NSCs can be expanded ex vivo and induced to differentiate into astrocytes, oligodendrocytes and functional neurons (Ciccolini et al., 1998; Johansson et al., 1999; Palmer et al., 1999; Reynolds et al., 1996; Ryder et al., 1990; Studer et al., 1996; Vescovi et al., 1993). In vivo, undifferentiated NSCs cultured for variable amounts of time eventually differentiate into glial cells, GABAergic and dopaminergic neurons (Flax et al., 1998; Gage et al., 1995; Suhonen et al., 1996). The most commonly used source of NSCs is allogeneic fetal brain. Alternatively, NSCs could be harvested from the autologous brain.

Stem cells of the present invention also include hematopoietic stem cells (HSCs). Bone marrow derived HSCs transplanted into mice incapable of developing cells of myeloid and lymphoid lineages migrated to brain and differentiated into cells that express neuron-specific antigens (Mezey, E. et al, 2000).

Yet another stem cell of the present invention is the mesenchymal stem cell (MSC), initially described by Fridenshtein (1982). A number of MSCs have been isolated. (See, for example, Caplan, A., et al., U.S. Pat. No. 5,486,359; Young, H., et al., U.S. Pat. No. 5,827,735; Caplan, A., et al., U.S. Pat. No. 5,811,094; Bruder, S., et al., U.S. Pat. No. 5,736,396; Caplan, A., et al., U.S. Pat. No. 5,837,539; Masinovsky, B., U.S. Pat. No. 5,837,670; Pittenger, M., U.S. Pat. No. 5,827,740; Jaiswal, N., et al., 1997; Cassiede P., et al., 1996; Johnstone, B., et al., 1998; Yoo, et al., 1998; Gronthos, S., 1994).

MSCs can also differentiate into ectodermal lineages, including neural, lineages (reviewed in Minguell, J. J. et al, 2001). Woodbury et al determined that bone marrow stromal cells of rodent and human origin can be induced to differentiate exclusively into neurons under certain conditions (Woodbury, D. et al, 2000). Studies by Sanchez-Ramos and coworkers also reported that human and mouse bone marrow stromal cells, when cultured in the presence of EGF or BDNF expressed nestin protein and mRNA, as well as glial fibrillary acidic protein, and the neuron-specific NeuN, all of which are markers for neural precursors (Sanchez-Ramos, J. et al, 2000).

The present invention is additionally described by way of the following illustrative, non-limiting Examples that provide a better understanding of the present invention and of its many advantages.

EXAMPLES

Example 1

Differentiation of Multipotent Adult Progenitor Cells (MAPC)

Bone marrow was collected from the femurs of 3-4 week-old 129× C57BL/6J ROSA26 mice according to guidelines from the University of Minnesota Institutional Animal Care and Use Committees. MAPCs were generated as described previously in Jiang and coworkers (Jiang, Y. et al, 2002). To demonstrate that cells were MAPCs, they were induced to differentiate to endothelium and hepatocyte-like cells as described (Schwartz, R. E. et al, 2002; Jiang, Y. et al, 2002). In addition, these cell populations were shown to contribute to most somatic cells of the mouse following blastocyst injection (Jiang, Y. et al, 2002).

MAPCs induced to differentiate into neuroectodermal lineage were cultured in base medium consisted of 60% Dulbecco's Modified Eagle's Medium-LG (Gibco-BRL, Grand Island, N.Y.), 40% MCDB-201 (Sigma Chemical Co, St Louis, Mo.) with 1× insulin-transferrin-selenium (ITS), 1× linoleic-acid-bovine-serum-albumin (LA-BSA), $10^{-9}$M dexamethasone (Sigma) and $10^{-4}$M ascorbic acid 2-phosphate (Sigma), 100 U penicillin and 1,000 U streptomycin (Gibco, Grand Island, N.Y.), on fibronectin (FN) (Sigma). In some instances, N2 supplement (Gibco) was also added. Cytokines that were added included 100 ng/mL basic fibroblast growth factor (bFGF), 100 ng/mL Sonic Hedgehog, 10 ng/mL FGF8, and 10 ng/mL BDNF (all from R&D Systems, Minneapolis, Minn.; all product literature relating to the same is herein incorporated by reference)

Astrocytes were prepared according to the following method. Mouse brain was dissected from e16 fetuses in Hanks Balanced Salt Solution (HBSS, Sigma). The dissected brain was minced and incubated in 0.125% trypsin/0.05% DNase (Sigma) in HBSS at 37° C. for 20 minutes. The tissue was triturated with a pipette and dissociated to a mixture of single cells and small cellular aggregates. After passing through a 70 µm nylon mesh, the astrocytic cells were centrifuged at 1000 rpm for 5 min and resuspended in DMEM+10% fetal bovine serum (FBS; Hyclone, Logan, Utah). Astrocytic cells were plated onto culture dishes, pre-coated with poly-D-lysine (100 µg/mL, Sigma) at 4° C. overnight, at a density of 600,000 cells/cm² until confluent.

After astrocytes had been cultured in DMEM+10% FBS for 8 days, culture medium was switched to serum free medium, supplemented with N2 supplement. Three days later, medium was collected as astrocyte conditioned medium.

MAPC-derived neurons were co-cultured with fetal brain astrocytes. Glass coverslips were coated with 500 µg/ml poly-D-lysine overnight at 4° C. Fetal brain astrocytes that were cultured for 8 days were trypsinized and re-plated on glass coverslips, and then allowed to grow to confluency. Once confluent, the coverslips were evaluated for presence of neurons by staining with antibodies against neurofilament (NF)-200 (see methods below) or placed upside down in cultures of MAPC-derived neuron-like cells. Cultures were maintained in serum free medium, supplemented with N2 supplement and without additional cytokines for 5-12 days.

Quantitative-RT-PCR (Q-RT-PCR) was performed to detect changes in levels of neuronal transcription factors and genes. RNA was extracted from MAPC differentiated for 5, 7, 10, 14, and 21 days, and brains from e18 or adult mice using the RNeasy kit (Qiagen, Valencia, Calif.). Two sequential steps of DNase (Invitrogen, Carlsbad, Calif.) treatment eliminated contaminating DNA. The resultant mRNA was reverse transcribed and cDNA underwent 40 rounds of amplification (ABI PRISM 7700, Perkin Elmer/Applied Biosystems) under the following reaction conditions: 40 cycles of a two step PCR (95° C. for 15 seconds, 60° C. for 60 seconds) after initial denaturation (95° C. for 10 minutes) with 2 µl of DNA solution, 1×SYBR Green PCR Master Mix reaction buffer (Applied Biosystems). Controls consisted of amplifications without reverse transcription and reactions without addition of cDNA template. Authenticity and size of PCR products were confirmed by melting curve analysis (using software provided by Perkin Elmer) and gel analysis. Primers used and size of expected products are shown in Table 1. mRNA levels were normalized using GAPDH as housekeeping gene, and compared with levels in e18 or adult mouse brain.

TABLE 1

Primers used for Q-RT-PCR

| | Gene | Forward | Reverse | Size | |
|---|---|---|---|---|---|
| (SEQ ID NO: 1) | Sox-1 | AAGATGCACAACTCGGAGATCAG | TGTAATCCGGGTGTTCCTTCAT | 51 bp. | (SEQ ID NO: 17) |
| (SEQ ID NO: 2) | Otx-2 | CCATGACCTATACTCAGGCTTCAGG | GAAGCTCCATATCCCTGGGTGGAAAG | 211 bp. | (SEQ ID NO: 18) |
| (SEQ ID NO: 3) | Otx-1 | AGGCGCTGTTCGCAAAGA | CCTCCTCGCGCATGAAGAT | 50 bp. | (SEQ ID NO: 19) |
| (SEQ ID NO: 4) | Pax-2 | CCAGGCATCAGAGCACATCA | CGTCTGTGTGCCTGACACATT | 141 bp. | (SEQ ID NO: 20) |
| (SEQ ID NO: 5) | Pax-5 | AAACGCAAGAGGGATGAAGGT | AACAGGTCTCCCCGCATCT | 100 bp. | (SEQ ID NO: 21) |
| (SEQ ID NO: 6) | Ptx-3 | TGTGTGGCACCTGGAGTTCA | CACCCTCAGGAACAGAGTGACTT | 107 bp. | (SEQ ID NO: 22) |
| (SEQ ID NO: 7) | CRet | GAGGAAATGTACCGTCTGATGCT | TCTTGACCATCATCTTCTCCAGATC | 102 bp. | (SEQ ID NO: 23) |
| (SEQ ID NO: 8) | Nurr-1 | TGAAGAGAGCGGAGAAGGAGATC | TCTGGAGTTAAGAAATCGGAGCTG | 255 bp. | (SEQ ID NO: 24) |
| (SEQ ID NO: 9) | Nestin | GAGAAGACAGTGAGGCAGATGAGTTA | GCCTCTGTTCTCCAGCTTGCT | 113 bp. | (SEQ ID NO: 25) |
| (SEQ ID NO: 10) | GFAP | GAGGAGTGGTATCGGTCTAAGTTTG | GCCGCTCTAGGGACTCGTT | 165 bp. | (SEQ ID NO: 26) |
| (SEQ ID NO: 11) | MBP | GTGCAGCTTGTTCGACTCCG | ATGCTCTCTGGCTCCTTGGC | 153 bp. | (SEQ ID NO: 27) |
| (SEQ ID NO: 12) | GABA | AGGTTGACCGTGAGAGCTGAAT | TGGGCAGGCATGGGC | 68 bp. | (SEQ ID NO: 28) |
| (SEQ ID NO: 13) | DAT | GCAATCATCACCACCTCCATTA | ATGGGCACATTGTGCTTCTG | 100 bp. | (SEQ ID NO: 29) |
| (SEQ ID NO: 14) | TH | AGTTCTCCCAGGACATTGGACTT | ACACAGCCCAAACTCCACAGT | 100 bp. | (SEQ ID NO: 30) |
| (SEQ ID NO: 15) | TrH | GGATGGAGTCTGATGTCACCAA | TGACGTTTCTCAGGCATTAAGC | 120 bp. | (SEQ ID NO: 31) |
| (SEQ ID NO: 16) | DBH | TTCCAATGTGCAGCTGAGTC | GGTGCACTTGCTTGTGCAGT | 242 bp. | (SEQ ID NO: 32) |

Cells were characterized for neuronal markers using immunophenotypic analysis. Cells were fixed with 4% paraformaldehyde (Sigma) for 4 minutes at room temperature, followed by methanol (Sigma) for 2 minutes at −20° C. For nuclear ligands, cells were permeabilized with 0.1 Triton-X-100 (Sigma) for 10 minutes. Slides were incubated sequentially for 30 minutes each with primary antibody, and fluorescein (FITC), Cy3 or Cy5 coupled anti-mouse-, goat- or rabbit-IgG antibodies. Between each step, slides were washed with PBS+1% BSA (Sigma). Cells were examined by confocal fluorescence microscopy (Confocal 1024 microscope; Olympus AX70, Olympus Optical Co. LTD, Japan). To assess the frequency of different cell types in a given culture, the number of cells staining positive with a given Ab were counted in four visual fields (50-200 cells per field).

Antibodies against myelin basic protein (MBP)(1:20), NF-200 (1:400), MAP2AB (1:400); tyrosine hydroxylase (TH; 1:1000), dopa-decarboxylase (DDC; 1:100), tryptophan hydroxylase (TrH; 1:250), gamma-aminobutyric acid (GABA; 1:500), control-mouse, -rabbit or -rat IgGs and FITC- or Cy3-labeled secondary Abs were from Sigma. Antibodies against Nestin (1:150) and Nurr1 (1:250) were from BD Transduction Laboratories (Lexington, Ky.). Antibodies directed against glial fibrillary acidic protein (GFAP, 1:400) were from DAKO Corporation (Carpinteria, Calif.) or Santa Cruz Biotechnology Inc (Santa Cruz, Calif.). Anti-dopamine antibodies (1:2000) were from Abcam Limited (Cambridge, UK). Polyclonal antibodies against Tau (1:400) were from Santa Cruz Biotechnology Inc. Cy5-labeled secondary antibodies were from Chemicon International (Temecula, Calif.).

Undifferentiated mMAPCs did not have neuroectodermal characteristics. No staining was seen with antibodies against nestin, GFAP, NF200, MBP, or neurotransmitters (not shown). By Q-RT-PCR, mMAPC did express low levels of c-Ret, Otx-2, and nestin mRNA, but no mRNA for sox1, otx2, Pax2, Pax5, Nurr1, GFAP, MBP, Dopamine, TH, GABA, TrH, or DBH (Table 2; '1' refers to mRNA isolated from fetal brain, while '2' refers to mRNA isolated from adult brain).

TABLE 2 mRNA levels on day 5, 7, 10, and 14 of differentiation of mMAPC to neuroectoderm

| Gene | Day 0 | Day 5 | Day 7 | Day 10 | Day 14 |
|---|---|---|---|---|---|
| Sox-1[1] | 0 | 0.57; 1.79; 2.22 | 0.58; 1.15; 2.14 | 0.68; 0.59; 5.58 | 0.9; ND; 1.74 |
| Otx-2[1] | 0 | 0.11; 0.25; 3.4 | 0.21; 0.06; 4.2 | 0.12; 0.08; 2.4 | ND; ND; 3.5 |
| Otx-1[1] | 0.01 | 0.33; 1.18; 7.06 | 0.36; 0.69; 32.1 | 0.26; 0.33; 24 | 1.67; ND; 5.31 |
| Pax-2[1] | 0 | 6.0; 8.2; 3.07 | 4.47; 7.06; 5.43 | 2.39; 1.64; 2.05 | 5.5; ND; 4.99 |
| Pax-5[1] | 0 | 0.11; 0.14; 0.9 | 0.13; 0.16; 3.75 | 0.05; 0.03; 1.84 | 0.48; ND; 1.33 |
| En-1[1] | 4.87 | 0.59; 1.45; 4.36 | 0.2; 0.8; 11.4 | 0.15; 0.32; 8 | 0.4; ND; 1.08 |
| cRet[2] | 0.14 | 2.84; 5.46; 15.7 | 2.19; 5.08; 72.8 | 2.53; 4.47; 54.2 | 24.17; ND; 36.9 |
| Nurr-1[2] | 0 | 0.55; 2.4; 0.38 | 1.12; 1.47; 1.11 | 1.41; 3.59; 1.6 | ND; ND; 1.68 |
| Nestin[1] | 0.52 | 27.3; 98.0; 50.4 | 10.2; 88.6; 70.8 | 5.9; 12.2; 243 | 6.48; ND; 14.7 |
| GFAP[2] | 0 | 0.56; 0.52; 1.05 | 0.36; 0.52; 3.26 | 1.32; 5.76; 21.0 | 11.75; ND; 9.19 |

TABLE 2-continued mRNA levels on day 5, 7, 10, and 14 of differentiation of mMAPC to neuroectoderm

| Gene | Day 0 | Day 5 | Day 7 | Day 10 | Day 14 |
|---|---|---|---|---|---|
| MBP[(2)] | 0 | 0.004; 0.006; 0.013 | 0.003; 0.008; 0.006 | 1.7; 4.08; 1.8 | 1.8; ND; 2.33 |
| GABA[(2)] | 0 | 1.36; 1.89; 6.23 | 0.99; 1.74; 17.5 | 7.8; 19.77; 94.0 | 61.8; ND; 69.6 |
| DAT[(2)] | 0 | 1.58; 4.39; 19.9 | 0.5; 2.83; 22.71 | 1.81; 5.66; 119 | 13.4; ND; 23.67 |
| TH[(2)] | 0 | 0.67; 1.31; 0.36 | 0.5; 1.2; 2.86 | 1.27; 3.94; 2.54 | 1.7; ND; 2.29 |
| TrH[(2)] | 0 | 0.49; 1.6; 0.46 | 0.51; 1.04; 4.99 | 1.56; 3.56; 7.14 | 3.92, ND; 3.81 |
| DBH[(1)] | 0 | 0 | 0 | 0 | 0 |

As neuroprogenitors can be expanded with PDGF-BB and induced to differentiate by removal of PDGF and addition of bFGF (Palmer, T. D. et al, 1999), undifferentiated MAPC were re-plated at 10,000 cells/cm$^2$ on FN coated plates or chamber slides, removed EGF, PDGF and LIF, but added 100 ng/mL bFGF. Q-RT-PCR of mMAPC treated with bFGF for 5 and 7 days demonstrated acquisition of neuroectodermal transcripts. On day 5 and 7, mRNA for sox1, otx2, otx1, pax2, pax5, and Nurr1 could be detected at levels between 0.1 and 7 fold those seen in fetal brain (n=3) (Table 2). By day 5 and 7, nestin mRNA levels increased to between 7 and 100 fold those in fetal brain (Table 2). Immunohistochemistry showed that by day 5, cells started to express nestin protein. By day 7, 65±11% of cells stained positive for nestin, 23±8% percent of nestin positive cells also expressed Nurr1 (n=3)(representative example shown in FIG. 1). By day 10, 62±7% of cells expressed NF200, 15±5% GFAP and 11±13% MBP (n=3) (representative example shown in FIG. 1), consistent with the finding that mRNA for GFPA and MBP increased to 1-4 fold over that detected in fetal brain. Double immunohistochemistry showed that GFAP, MBP, and NF200 were never detected in the same cells.

When mMAPC were cultured sequentially with 100 ng/mL bFGF for 7 days, followed by a combination of 10 ng/mL FGF-8 and 100 ng/mL SHH for 7 days and finally 10 ng/mL BDNF for 7 days, the latter in medium also supplemented with N2 medium, a more mature phenotype was seen. Q-RT-PCR demonstrated that by day 10 and 14 levels of GABA, dopamine and TH, and TrH mRNA increased between 1.7 and 120 fold. Immunophenotypic analysis on day 21 showed that 25±7% of cells expressed markers of dopaminergic neurons (shown DDC and TH; also dopamine), 18±3% of serotonergic (TrH) and 52±5% of GABA-ergic (GABA) neurons (n=3)(representative example shown in FIG. 1). Neuron-like cells became polarized, as Tau and MAP2AB were expressed in axonal and somatodendritic compartments respectively. Fewer than 10% of cells stained positive for astrocytes or oligodendrocyte markers (not shown). Consistent with the immunohistological analyses, the levels of MBP and GFAP mRNA decreased by d21 (not shown).

Example 2

Maturation of Murine Multipotent Adult Progenitor Cells

Murine MAPCs were seeded at a density of 10$^5$ cells/well in 6-well tissue culture plates in 1 ml of MAPC culture medium, 1 ml of supernatant of the 293 cell line transfected with a third generation, VSV-g pseudotyped e-GFP-expressing lentivirus (107 infectious particles/mL) (a kind gift from Dr. Thierry Vandendriesche, Katholieke Universiteit Leuven, Belgium) and polybrene (8 μg/mL final concentration), was added to the wells. After 6 hours of incubation at 37° C. and 5% $CO_2$, the medium was replaced with fresh MAPC medium. Transduction of MAPCs was repeated 3 times. Transduction efficiency of the final population was 28% as determined by counting 200 cells.

Figure 2:
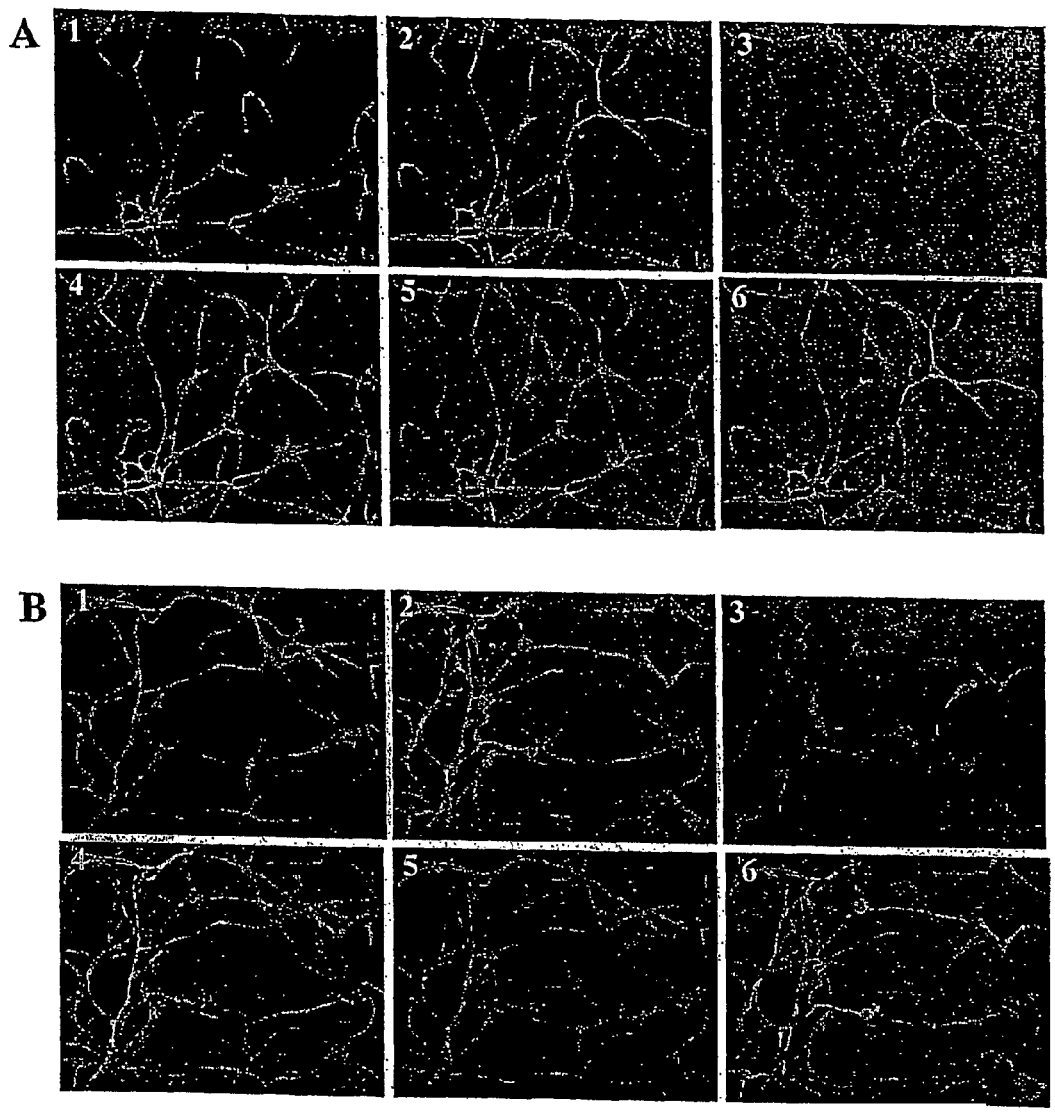
FIG. 2A shows cells labeled with antibodies against GABA and DDC: Photos 1-3 show single fluorescence color analysis: (1) cells stained with antibodies against GABA followed by secondary Cy3 coupled antibody; (2) eGFP labeled cells; (3) cells stained with antibodies against DDC followed by secondary Cy5 coupled antibody; Photos 4-6 represent overlay pictures: (4) GFP/anti-GABA-Cy3; (5) anti-GABA Cy3/Anti-DDC-Cy5; (6) GFP/anti-DDC-Cy5. Shown are GFP positive cells that have acquired morphological and phenotypic features of GABA-ergic and dopaminergic neurons, whereas a fraction of cells with morphological and phenotypic features of GABA-ergic and dopaminergic neuron was GFP negative.
FIG. 2B show cells labeled with antibodies against TrH and Dopamine: Photos 1-3 represent single fluorescence color analysis: (1) cells stained with antibodies against TrH followed by secondary Cy3 coupled antibody; (2) eGFP labeled cells; (3) cells stained with antibodies against dopamine followed by secondary Cy5 coupled antibody; Photos 4-6 represent overlay pictures: (4) GFP/anti-TrH-Cy3; (5) anti-TrH-Cy3/Anti-dopamine-Cy5; (6) GFP/anti-dopamine-Cy5. Shown are GFP positive cells that have acquired morphological and phenotypic features of serotonergic and dopaminergic neurons, whereas a fraction of cells with morphological and phenotypic features of serotonergic and dopaminergic neurons was GFP negative.

Based on studies by Wagner et al (Wagner, J. et al, 1999) and Song et al (Song, H. et al, 2002), we next tested whether cultured neuron-like cells could be maintained in vitro for more extended periods of time to allow further maturation, when cultured in the presence of fetal brain astrocytes. Astrocytes were cultured from e16 fetal brain in 10% FCS. After several passages, no neural cells could be detected by immunofluorescence microscopy (not shown). In initial studies, astrocyte conditioned medium was added to the developing neuroectodermal cells generated from MAPC. However, no significant further morphologic maturation was observed (n=2)(not shown). In subsequent experiments, astrocytes were plated onto coverslips and allowed to grow to confluence. Coverslips were placed upside down in chamberslides in which eGFP-transduced MAPC had been cultured for 7 days with bFGF, 7 days with FGF8+SHGH and 7 days with BDNF in N2 medium. After an additional 5-12 days in culture, eGFP-expressing MAPC-derived neuron-like cells were again evaluated by immunofluorescence and we demonstrated that eGFP positive cells, continued to express markers of dopaminergic neurons (~25% TH and dopamine), serotonergic neurons (~25%, TrH) and GABA-ergic neurons (~50% GABA) and acquired a much more mature neural morphology with a more elaborate array of axons (n=3; representative example shown in FIG. 2).

eGFP transduced mouse MAPC (28% transduction efficiency) were cultured on fibronectin coated chamber slides sequentially for 7 days with 100 ng/mL bFGF, 10 ng/mL FGF8 and 100 ng/mL SHH, 10 ng/mL BDNF, and finally, with e16 fetal mouse brain astrocytes plated on coverslips that were placed upside down in the chamber slides. After a total of 28 days, cells were fixed and stained. Slides were analyzed for presence of GFP positive cells, and cells co-staining with Cy3 or Cy5 labeled antibodies.

Example 3

Patch-Clamp Electrophysiology of Differentiated Multipotent Adult Progenitor Cells Standard, whole-cell patch-clamp recording methodologies were used to examine the physiological properties of cultured bone marrow stem cells. Voltage-clamp and current-clamp recordings were obtained using a Dagan 3900A patch-clamp amplifier (Dagan Corporation, Minneapolis), that was retrofitted with a Dagan 3911 expander unit. Patch pipettes, made from borosilicate glass, were pulled on a Narishige pipette puller (model PP-83). The pipettes were filled with an intracellular saline which consisted of the following (in mM):

142.0 KF, 7.0 $Na_2SO_4$, 3.0 $MgSO_4$, 1.0 $CaCl_2$, 5.0 HEPES, 11.0 EGTA, 1.0 glutathione, 2.0 glucose, 1.0 ATP (magnesium salt), 0.5 GTP (sodium salt)(Sigma). For most recordings, the fluorescent dye 5,6-carboxyfluorescein (0.5 mM; Eastman Kodak Chemicals) was also added to the pipette solution for the purpose of confirming visually, using fluorescence microscopy, that the whole-cell patch recording configuration had been achieved. Pipette resistances ranged from 11 to 24 MOhm. The standard extracellular recording saline was comprised of the following (in mM): 155 mM NaCl, 5.0 mM KCl, 1.8 mM $CaCl_2$, 1.0 mM $MgCl_2$, 10 mM HEPES, 5 mM glucose (Sigma).

For some experiments 1 µM tetrodotoxin (TTX) was added to the standard control solution. The pH of the intracellular and extracellular recording solutions was adjusted to 7.4 and 7.8, respectively. Unless otherwise noted, all chemical compounds were obtained through the Sigma (St. Louis) chemical company. PClamp 8.0 (Axon Instruments, Foster City) was used to run experiments, and to collect and store data. The data presented herein were corrected for a 8.4 mV liquid junctional potential, which was calculated using the JPCALC software package (Barry, P. H., 1994). Off-line analyses and graphical representations of the data were constructed using Clampfit 8.0 (Axon Instruments, Foster City) and Prism (Graphpad, San Diego).

Patch-clamp recordings were obtained from 50 MAPCs from 5 independent cultures. Recordings were made from cells that were cultured for 7 days each with bFGF, FGF8b and SHH, and BDNF followed by either co-culture with astrocytes for 5 (n=9), 7 (n=9), 8 (n=14), 9 (n=9), and 12 (n=2) days, or that were incubated for 7 days with conditioned media from cultures of fetal brain astrocytes (n=7). At all time points, the resting membrane potentials (RMP) of cells co-cultured with astrocytes were variable, ranging between −8.4 and −55.4 mV. However, RMPs tended to become more negative as a function of time in culture with astrocytes. The median RMPs were −27.4, −33.7, −41.9, and −44.4 mV after 5, 7, 8, and 9 days, respectively, in co-culture. Input resistance also varied considerably across cells (range=0.133 to 9.8 GOhm), however, no trend was apparent in the value of input resistance as a function of time the cells spent in culture with astrocytes (median input resistance=2.4, 1.6, 2.4 and 1.2 GOhm after 5, 7, 8, and 9 days in culture with astrocytes, respectively).

Figure 3:
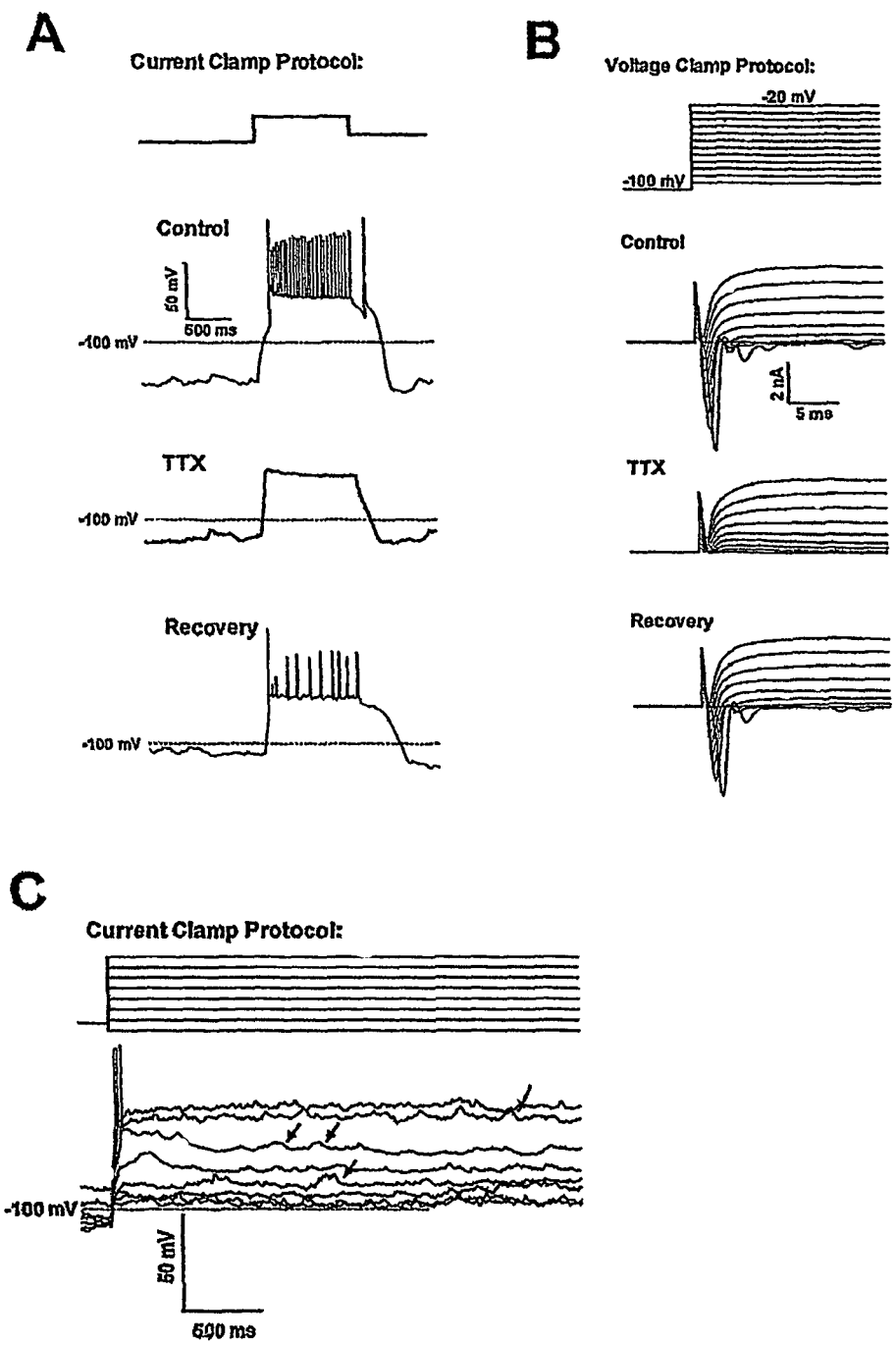
FIG. 3A shows spiking behavior and voltage-gated currents from MAPCs in co-culture with fetal mouse brain astrocytes. Current-clamp recordings are from a MAPC that had been co-cultured with astrocytes for 8 days. Illustrated in the lower three panels are the voltage responses elicited by the current injection protocol shown (a 17 pA current injection step; top panel). The repetitive spiking recorded in this cell was blocked reversibly by tetrodotoxin (TTX). The current injection protocol reports the current injected relative to a negative DC current which was injected into the cell for the purpose of "holding" it near −100 to −130 mV.
FIG. 3B shows voltage-clamp recordings of leak subtracted currents from the same cell as shown in A. The top panel illustrated the voltage-clamp protocol used to elicit the families of currents shown in the lower three panels. A large transient inward current was evident, and this could be blocked reversibly by TTX.
FIG. 3C shows current-clamp records obtained from a MAPC that had been co-cultured with astrocytes for 8 days. In this representative, the cell produced only one spike in response to depolarizing current injections (ΔpA=7). The arrows point to possible synaptic potentials.

Current-clamp recordings demonstrated that spiking was observed in cells that were co-cultured with astrocytes at all time points examined. FIG. 3A illustrates an example of spiking behavior evoked from a cell that had been co-culture with astrocytes for 8 days. Interestingly, the proportion of cells studied which were capable of generating action potentials increased dramatically after day 5 in culture with astrocytes. Twenty-two percent of cells that were co-cultured with astrocytes for only spiked for 5 days. In contrast, after day 5, spiking cells represented between 71% and 100% of cells studied at each time period. Voltage-clamp experiments showed that spiking MAPC expressed a rapidly inactivating inward current. This transient inward current generally could not be elicited from cells, which failed to produce a spike in current-clamp experiments (a small transient inward current was observed in only 1 of the non-spiking MAPC).

FIG. 3B shows the inward sodium current, which was elicited from the same cells as in 3A. Approximately 67 percent of spiking cells could be made to spike repetitively in response depolarizing current injection steps; the other 33 percent of cells generated only a single action potential with varying amounts of depolarizing current stimulation. Where examined, the spiking behavior and transient inward currents were blocked by TTX (see panels labeled TTX in FIGS. 3A and B). All cells examined that were co-cultured with astrocytes had outward currents, however, the identities of those currents remain to be determined. Voltage and current traces from our patch-clamp recordings also suggested the occurrence of synaptic events (FIG. 3C, see arrows).

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the following claims below.

REFERENCES

Abraham, J. A.; Whang, J. L.; Tumolo, A.; Mergia, A.; Friedman, J.; Gospodarowicz, D.; Fiddes, J. C.: "Human basic fibroblast growth factor: nucleotide sequence and genomic organization." (1986) EMBO J. 5: 2523-2528.

Alison, M., and Sarraf, C.: "Hepatic stem cells" (1998) J. Hepatol. 29: 678-83.

Alonso-Vanegas, M. A., Fawcett, J. P., Causing, C. G., Miller, F. D. & Sadikot, A. F.: "Characterization of dopaminergic midbrain neurons in a DBH:BDNF transgenic mouse" (1999) J Comp Neurol 413, 449-62.

Asahara, T., Murohara, T., Sullivan, A., Silver, M., van der Zee, R., Li, T., Witzenbichler, B., Schatteman, G. & Isner, J.: "Isolation of putative progenitor endothelial cells for angiogenesis" (1997) Science 275, 964-967.

Barry, P. H.: "JPCalc, a software package for calculating liquid junction potential corrections in patch-clamp, intracellular, epithelial and bilayer measurements and for correcting junction potential measurements" (1994) J. Neurosci. Meth. 51: 107-16.

Batchelor, P. E., Liberatore, G. T., Porritt, M. J., Donnan, G. A. & Howells, D. W.: "Inhibition of brain-derived neurotrophic factor and glial cell line-derived neurotrophic factor expression reduces dopaminergic sprouting in the injured striatum" (2000) Eur J Neurosci 12, 3462-8.

Bjornson, C., Rietze, R., Reynolds, B., Magli, M. & Vescovi, A.: "Turning brain into blood: a hematopoietic fate adopted by adult neural stem cells in vivo" (1999) Science 283, 354-7.

Brazelton, T. R., Rossi, F. M. V., Keshet, G. I. & Blau, H. E.: "From Marrow to Brain: Expression of Neuronal Phenotypes in Adult Mice" (2000) Science 290, 1775-1779.

Bruder, S., et al., U.S. Pat. No. 5,736,396

Caplan, A., et al., U.S. Pat. No. 5,486,359

Caplan, A., et al., U.S. Pat. No. 5,811,094

Caplan, A., et al., U.S. Pat. No. 5,837,539

Cassiede P., Dennis, J. E., Ma, F., Caplan, A. I.: "Osteochondrogenic potential of marrow mesenchymal progenitor cells exposed to TGF-beta 1 or PDGF-BB as assayed in vivo and in vitro". (1996) J Bone Miner Res. 9:1264-73.

Cattaneo, E. & McKay, R.: "Proliferation and differentiation of neuronal stem cells regulated by nerve growth factor" (1990) Nature 347, 762-5.

Cazorla, P., Smidt, M. P., O'Malley, K. L. & Burbach, J. P.: "A response element for the homeodomain transcription factor Ptx3 in the tyrosine hydroxylase gene promoter" (2000) J Neurochem. 74, 1829-37.

Ciccolini, F., and Svendsen, C. N.: "Fibroblast growth factor 2 (FGF-2) promotes acquisition of epidermal growth factor (EGF) reponsiveness in mouse striata] precursor cells: Identification of neural precursors responding to both EGF and FGF-2". (1998) J Neuroscience 18:7869-7880.

Clarke, D. L., Johansson, C. B., Wilbertz, J., Veress, B., Nilsson, E., Karlstrom, H., Lendahl, U., and Frisen, J.: "Generalized potential of adult NSCs". (2000) *Science* 288:1660-3.

Danielian, P. S. & McMahon, A. P.: "Engrailed-1 as a target of the Wnt-1 signalling pathway in vertebrate midbrain development" (1996) *Nature* 383, 332-4.

DiGuisto, et al., U.S. Pat. No. 5,681,599

Doetsch, F., Caille, I., Lim, D. A., Garcia-Verdugo, J. M., and Alvarez-Buylla, A.: "Subventricular zone astrocytes are NSCs in the adult mammalian brain". (1999) *Cell* 97:703-716

Donovan, P. J. and Gearhart, J.: "The end of the beginning for pluripotent stem cells" (2001) *Nature* 414: 92-97.

Fei, R., et al., U.S. Pat. No. 5,635,387

Ferrari, G., Cusella-De Angelis, G., Coletta, M., Paolucci, E., Stornaiuolo, A., Cossu, G. & Mavilio, F.: "Muscle regeneration by bone marrow-derived myogenic progenitors" (1998) *Science* 279, 528-30.

Flax, J. D., Sanjay, A., Yang, C., Simonin, C., Wills, A. M., Billinghurst, L. L., Jendoubi, M., Sidman, R. L., Wolfe, J. H., Kim, S. E., and Snyder, E. Y.: "Engraftable human NSCs respond to developmental cues replace neurons and express foreign genes". (1998) *Nature Biotechnol* 16:1033-1038.

Fridenshtein, A.: "Stromal bone marrow cells and the hematopoietic microenvironment". (1982) *Arkh Pathol* 44:3-11.

Furcht et al. International Application No. PCT/US00/21387

Gage, F., Coates, P., Palmer, T., Kuhn, H., Fisher, L., Suhonen, J., Peterson, D., Suhr, S., and Ray, J.: "Survival and differentiation of adult neuronal progenitor cells transplanted to the adult brain". (1995) *Proc Natl Acad Sci USA* 92:11879-83.

Gage, F. H. (2000). Mammalian NSCs. *Science* 287:1433-1438

Gemel, J.; Gorry, M.; Ehrlich, G. D.; MacArthur, C. A.:
Structure and sequence of human FGF8. Genomics 35: 253-257, 1996.

Gloster, A., Wu, W., Speelman, A., Weiss, S., Causing, C., Pozniak, C., Reynolds, B., Chang, E., Toma, J. G. & Miller, F.: "The T alpha 1 alpha-tubulin promoter specifies gene expression as a function of neuronal growth and regeneration in transgenic mice" (1994) *J Neurosci.* 14, 7319-30.

Gritti, A., Frolichsthal-Schoeller, P., Galli, R., Parati, E., Cova, L., Pagano, S., Bjornson, C. & Vescovi, A.: "Epidermal and fibroblast growth factors behave as mitogenic regulators for a single multipotent stem cell-like population from the subventricular region of the adult mouse forebrain" (1999) *J Neurosci* 19, 3287-97.

Gronthos, S., Graves, S., Ohta, S., and Simmons, P.: "The STRO-1+ fraction of adult human bone marrow contains the osteogenic precursors". (1994) *Blood* 84: 4164-73.

Gussoni, E., Soneoka, Y., Strickland, C., Buzney, E., Khan, M., Flint, A., Kunkel, L. & Mulligan, R.: "Dystrophin expression in the mdx mouse restored by stem cell transplantation" (1999) *Nature* 401, 390-4.

Hill, B., Rozler, E., Travis, M., Chen, S., Zannetino, A., Simmons, P., Galy, A., Chen, B., Hoffman, R.: "High-level expression of a novel epitope of CD59 identifies a subset of CD34+ bone marrow cells highly enriched for pluripotent stem cells". (1996) *Exp Hematol.* 8:936-43.

Hyman, C., Hofer, M., Barde, Y., Juhasz, M., Yancopoulos, G., Squinto, S. & Lindsay, R.: "BDNF is a neurotrophic factor for dopaminergic neurons of the substantia nigra" (1991) *Nature* 350, 230-2.

Jackson, K., Mi, T. & Goodell, M. A.: "Hematopoietic potential of stem cells isolated from murine skeletal muscle" (1999) *Proc Natl Acad Sci USA* 96, 14482-6.

Jackson, K., Majka, S. M., Wang, H., Pocius, J., Hartley, C., Majesky, M. W., Entman, M. L., Michael, L., Hirschi, K. K. & M. A., G. "Regeneration of ischemic cardiac muscle and vascular endothelium by adult stem cells" (2001) *J Clin Invest* 107, 1395-1402.

Jaiswal, N., Haynesworth, S. E., Caplan, A. I., Bruder, S. P.: "Osteogenic differentiation of purified, culture-expanded human mesenchymal stem cells in vitro" (1997) *J. Cell Biochem.* 64(2): 295-312.

Jiang, Y., Vaessen, B., Lenvik, T., Blackstad, M., Reyes, M. & Verfaillie, C. M.: "Multipotent progenitor cells can be isolated from postnatal murine bone marrow, muscle, and brain" (2002) *Exp Hematol.* 30(8): 896-904.

Jiang, Y., Jahagirdar, B., Reyes, M., Reinhardt, R. L., Schwartz, R. E., Chang, H.-C., Lenvik, T., Lund, T., Blackstad, M., Du, J., Aldrich, S., Lisberg, A., Kaushal, S., Largaespada, D. L. & Verfaillie, C. M.: "Pluripotency of mesenchymal stem cells derived from adult marrow" (2002) *Nature* 418, 41-9.

Johansson, C. B., Momma, S., Clarke, D. L., Risling, M., Lendahl, U. & Frisen, J.: "Identification of a NSC in the adult mammalian central nervous system" (1999) *Cell* 96, 25-34.

Johnstone, B., Hering, T. M., Caplan, A. I., Goldgberg, V. M., Yoo, J. U.: "In vitro chondrogenesis of bone marrow-derived mesenchymal progenitor cells". (1998) *Exp Cel Res.* 1:265-72.

Kawada, H. & Ogawa, M.: "Bone marrow origin of hematopoietic progenitors and stem cells in murine muscle" (2001) *Blood* 98, 2008-13.

Kawasaki, H., Mizuseki, K., Nishikawa, S., Kaneko, S., Kuwana, Y., Nakanishi, S., Nishikawa, S. I. & Sasai, Y.: "Induction of midbrain dopaminergic neurons from ES cells by stromal cell-derived inducing activity" (2000) *Neuron* 28, 31-40.

Keene, C. D., Ortiz-Gonzalez, X. R., Jiang, Y., Largaespada, D. A., Verfaillie, C. M. & Low, W. C. (2003) In Press.

Kim, J. H., Auerbach, J. M., Rodriguez-Gomez, J. A., Velasco, I., Gavin, D., Lumelsky, N., Lee, S. H., Nguyen, J., Sanchez-Pernaute, R., Bankiewicz, K. & McKay, R.: "Dopamine neurons derived from embryonic stem cells function in an animal model of Parkinson's disease" (2002) *Nature* 418, 50-6.

Kopen, G., Prockop, D., and Phinney, D.: "Marrow stromal cells migrate throughout forebrain and cerebellum, and they differentiate into astrocytes after injection into neonatal mouse brains". (1999) *Proc Natl Acad Sci USA.* 96:10711-10716.

Krause, D. S., Theise, N. D., Collector, M. I., Henegariu, O., Hwang, S., Gardner, R., Neutzel, S. & Sharkis, S. I.: "Multi-organ, multi-lineage engraftment by a single bone marrow-derived stem cell" (2001) *Cell* 105, 369-77.

Lagasse, E., Connors, H., Al-Dhalimy, M., Reitsma, M., Dohse, M., Osborne, L., Wang, X., Finegold, M., Weissman, I. L. & Grompe, M.: "Purified hematopoietic stem cells can differentiate into hepatocytes in vivo" (2000) *Nat Med.* 6, 1229-34.

Lebkowski, J. S., Gold, J., Xu, C., Funk, W., Chiu, C. P., and Carpenter, M. K.: "Human embryonic stem cells: culture, differentiation, and genetic modification for regenerative medicine applications" (2001) *Cancer J* 7 (Suppl. 2): S83-93.

Lee, S. H., Lumelsky, N., Studer, L., Auerbach, J. M. & McKay, R. D.: "Efficient generation of midbrain and hindbrain neurons from mouse ES cells" (2000) *Nat Biotechnol* 18, 675-9.

Lendahl, U., Zimmerman, L. B. & McKay, R. D.: "CNS stem cells express a new class of intermediate filament protein" (1990) *Cell* 60, 585-95.

Lim, J. W., and Bodnar, A.: "Proteome analysis of conditioned medium from mouse embryonic fibroblast feeder layers which support the growth of human embryonic stem cells" (2002) *Proteomics* 2(9): 1187-1203.

Lin, Y., Weisdorf, D. J., Solovey, A. & Hebbel, R. P.: "Origins of circulating endothelial cells and endothelial outgrowth from blood" (2000) *J Clin Invest* 105, 71-7.

Lovell-Badge, R.: "The future for stem cell research" (2001) *Nature* 414: 88-91.

Martin, G. R.: "Isolation of a pluripotent cell line from early mouse embryos cultured in medium conditioned by teratocaracinoma stem cells". (1981) *Proc Natl Acad Sci U.S.A.* 12:7634-8.

Marigo, V.; Roberts, D. J.; Lee, S. M. K.; Tsukurov, O.; Levi, T.; Gastier, J. M.; Epstein, D. J.; Gilbert, D. J.; Copeland, N. G.; Seidman, C. E.; Jenkins, N. A.; Seidman, J. G.; McMahon, A. P.; Tabin, C.: Cloning, expression, and chromosomal location of SHH and IHH: two human homologues of the Drosophila segment polarity gene hedgehog. (1995) Genomics 28: 44-51.

Masinovsky, B., U.S. Pat. No. 5,837,670

Maisonpierre, P. C.; Le Beau, M. M.; Espinosa, R., III; Ip, N. Y.; Belluscio, L.; de la Monte, S. M.; Squinto, S.; Furth, M. E.; Yancopoulos, G. D.: Human and rat brain-derived neurotrophic factor and neurotrophin-3: gene structures, distributions and chromosomal localizations. (1991) Genomics 10: 558-568.

McGlave, et al., U.S. Pat. No. 5,460,964

McKinney-Freeman, S. L., Jackson, K. A., Camargo, F. D., Ferrari, G., Mavilio, F. & Goodell, M. A.: "Muscle-derived hematopoietic stem cells are hematopoietic in origin" (2002) *Proc Natl Acad Sci USA* 99, 1341-6.

Mezey, E., Chandross, K. J., Harta, G., Maki, R. A., & McKercher, S. R.: "Turning Blood into Brain: Cells Bearing Neuronal Antigens Generated in vivo from Bone Marrow" (2000) *Science* 290, 1779-1782.

Minguell, J. J., Erices, A., and Conget, P.: "Mesenchymal Stem Cells" (2001) *Exp. Biol. Med.* 226(6): 507-520.

Morrison, S. J., White, P. M., Zock, C., and Anderson, D. J.: "Prospective identification isolation by flow cytometry and in vivo self-renewal of multipotent mammalian neural crest stem cells". (1999) *Cell.* 96:737-749.

Okabe, S., Forsberg-Nilsson, K., Spiro, A. C., Segal, M., and McKay, R. D.: "Development of neuronal precursor cells and functional postmitotic neurons from ES cells in vitro" (1996) *Mech Dev* 59:89-102.

Orkin, S.: "Embryonic stem cells and transgenic mice in the study of hematopoiesis". (1998) *Int. J. Dev. Biol.* 42:927-34.

Orlic, D., Kajstura, J., Chimenti, S., Jakoniuk, I., Anderson, S. M., Li, B., Pickel, J., McKay, R., Nadal-Ginard, B., Bodine, D. M., Leri, A. & Anversa, P.: "Bone marrow cells regenerate infarcted myocardium" (2001) *Nature* 410, 701-5.

Palmer, T. D., Markakis, E. A., Willhoite, A. R., Safar, F., and Gage, F. H.: "Fibroblast growth factor-2 activates a latent neurogenic program in NSCs from diverse regions of the adult CNS." (1999) *J Neurosci* 19:8487-97.

Panchision, D. M., Martin-DeLeon, P. A., Takeshima, T., Johnston, J. M., Shimoda, K., Tsoulfas, P., McKay, R. D. & Commissiong, J. W.: "An immortalized, type-1 astrocyte of mesencephalic origin source of a dopaminergic neurotrophic factor" (1999) *J Mol Neurosci.* 11, 209-21.

Perrone-Capano, C. & Di Porzio, U.: "Genetic and epigenetic control of midbrain dopaminergic neuron development" (2000) *Int J Dev Biol* 44, 679-87.

Pesce, M. and Scholer, H. R.: "Oct-4: control of totipotency and germline determination" (2000) *Mol. Reprod. Dev.* 55: 452457.

Petersen, B. E., Bowen, W. C., Patrene, K. D., Mars, W. M., Sullivan, A. K., Murase, N., Boggs, S. S., Greenberger, J. S. & Goff, J. P.: "Bone marrow as a potential source of hepatic oval cells" (1999) *Science* 284, 1168-1170.

Pittenger, M. F., Mackay, A. M., Beck, S. C., Jaiswal, R. K., Douglas, R., Mosca, J. D., Moorman, M. A., Simonetti, D. W., Craig, S., and Marshak, D. R.: "Multilineage potential of adult human MSCs". (1999) *Science* 284: 143-147 Pittenger, M., U.S. Pat. No. 5,827,740

Potten, C.: "Stem cells in gastrointestinal epithelium: numbers, characteristics and death". (1998) *Philos Trans R Soc Lond B Biol Sci* 353: 821-30.

Rafli, S., Shapiro, F., Rimarachin, J., Nachman, R., Ferris, B., Weksler, B., Moore, M. & Asch, A.: "Human bone marrow microvascular endothelial cells support long-term proliferation and differentiation of myeloid and megakaryocytic progenitors" (1994) *Blood* 84, 10.

Reubinoff, B. E., Pera, M. F., Fong, C. Y., Trounson, A., and Bongso, A.: "ES cell lines from human blastocysts: somatic differentiation in vitro". (2000) *Nat Biotech* 18:399-404.

Reynolds, B., and Weiss, S.: "Generation of neurons and astrocytes from isolated cells of the adult mammalian central nervous system". (1992) *Science* 255: 1707-10.

Reynolds, B., and Weiss, S.: "Clonal and population analyses demonstrate that an EGF-responsive mammalian embryonic CNS precursor is a stem cell". (1996) *Dev Biol* 175: 1-13.

Richards, L. J., Kilpatrick, T. J. & Bartlett, P. F.: "De novo generation of neuronal cells from the adult mouse brain" (1992) *Proc Natl Acad Sci USA.* 89, 8591-5.

Rowitch, D. H. & McMahon, A. P.: "Pax-2 expression in the murine neural plate precedes and encompasses the expression domains of Wnt-1 and En-1" (1995) *Mech Dev* 52, 3-8.

Roy, N. S., Wang, S., Jiang, L., Kang, J., Benraiss, A., Harrison-Restelli, C., Fraser, R. A., Couldwell, W., Kawaguchi, A., Okano, H., Nedergaard, M. & Goldman, S. A.: "In vitro neurogenesis by progenitor cells isolated from the adult human hippocampus" (2000) *Nat Med* 6, 271-7.

Ryder, E. F., Snyder, E. Y., and Cepko, C. L.: "Establishment and characterization of multipotent neural cell lines using retrovirus vector-mediated oncogene transfer". (1990) *J Neurobiol* 21: 356-375.

Sanchez-Ramos, J., Song, S., Cardozo-Pelaez, F., Hazzi, C., Stedeford, T., Willing, A., Freeman, T. B., Saporta, S., Janssen, W., Patel, N., Cooper, D. R., and Sanberg, P. R.: "Adult bone marrow stromal cells differentiate into neural cells in vitro". (2000) *Exp Neurol.* 164:247-56

Saucedo-Cardenas, O., Quintana-Hau, J. D., Le, W. D., Smidt, M. P., Cox, J. J., De Mayo, F., Burbach, J. P. & Conneely, 0. M.: "Nurr1 is essential for the induction of the dopaminergic phenotype and the survival of ventral mesencephalic late dopaminergic precursor neurons" (1998) *Proc Natl Acad Sci USA* 95, 4013-8.

Schwartz, et al., U.S. Pat. No. 759,793

Schwartz, R. E., Reyes, M., Koodie, L., Jiang, Y., Blackstad, M., Johnson, S., Lund, T., Lenvik, T., Hu, W. S. and Verfaillie, C. M.: "Multipotent adult progenitor cells from bone marrow differentiate into functional hepatocyte-like cells" (2002) *J Clin Invest.* 96, 1291-1302.

Seale, P., Sabourin, L. A., Girgis-Gabardo, A., Mansouri, A., Gruss, P., Rudnicki, M. A.: "Pax7 is required for the specification of myogenic satellite cells" (2000) *Cell* 102(6): 777-86.

Shamblott, M., Axelman, J., Wang, S., Bugg, E., Littlefield, J., Donovan, P., Blumenthal, P., Huggins, G., Gearhart, J.: "Derivation of pluripotent stem cells from cultured human primordial germ cells". (1998) *Proc. Natl. Acad. Sci. U.S.A.* 95: 13726-31.

Shih, C. C., Weng, Y., Mamelak, A., LeBon, T., Hu, M. C. & Forman, S.: "Identification of a candidate human neurohematopoietic stem-cell population" (2001) *Blood* 98, 2412-22.

Simeone, A.: "Otx1 and Otx2 in the development and evolution of the mammalian brain" (1998) *EMBO J* 117, 6790-8.

Simmons, P., et al., U.S. Pat. No. 5,677,136

Smidt, M. P., van Schaick H. S., Lanctot, C., Tremblay, J. J., Cox, J. J., an der Kleij, A., Wolterink, G., Drouin, J. & Burbach, J. P.: "A homeodomain gene Ptx3 has highly restricted brain expression in mesencephalic dopaminergic neurons" (1997) *Proc Natl Acad Sci USA* 94, 13305-10.

Song, H., Stevens, C. F. & Gage, F. H.: "Astroglia induce neurogenesis from adult neural stem cells" (2002) *Nature* 417: 39-44.

Soule, H. D., Vazguez, J., Long, A., Albert, S., and Brennan, M.: "A human cell line from a pleural effusion derived from a breast carcinoma." (1973) *J. Natl. Cancer Inst.* 51(5): 1409-16

Storch, A., and Schwarz, J.: "Neural stem cells and Parkinson's disease" (2002) *J. Neurol.* 249(Suppl. 3): III/30-III/32.

Stoykova, A. & Gruss, P.: "Roles of Pax-genes in developing and adult brain as suggested by expression patterns" (1994) *J Neurosci,* 14 (3 Pt. 2): 1395-1412.

Strom, T. B., Field, L. J., and Ruediger, M.: "Allogeneic stem cells, clinical transplantation, and the origins of regenerative medicine" (2002) *Curr. Opin. Immunol.* 14: 601-605.

Studer, L., Spenger, C., Seiler, R., Othberg, A., Lindvall, O. & Odin, P.: "Effects of brain-derived neurotrophic factor on neuronal structure of dopaminergic neurons in dissociated cultures of human fetal mesencephalon" (1996) *Exp Brain Res* 108, 328-36.

Suhonen, J., Peterson, D., Ray, J., and Gage, F.: "Differentiation of adult hippocampus-derived progenitors into olfactory neurons in vivo". (1996) *Nature* 383:624-7.

Svendsen, C. N., Caldwell, M. A., Ostenfeld, T.: "Human neural stem cells: Isolation, expansion and transplantation". (1999) *Brain Path* 9:499-513.

Takahashi, T., Takahashi, K., Mernaugh, R., Drozdoff, V., Sipe, C., Schoecklmann, H., Robert, B., Abrahamson, D. R., Daniel, T. O.: "Endothelial localization of receptor tyrosine phosphatase, ECRTP/DEP-1, in developing and mature renal vasculature" (1999) *J. Am. Soc. Nephrol.* 10(10): 2135-45.

Temple, S.: "The development of neural stem cells" (2001) *Nature* 414: 112-117.

Terada, N., Hamazaki, T., Oka, M., Hoki, M., Mastalerz, D. M., Nakano, Y., Meyer, E. M., More, L. 1., Petersen, B. E. & Scott, E. W.: "Bone marrow cells adopt the phenotype of other cells by spontaneous cell fusion" (2002) *Nature* 416, 542-5 Theise, N. D., Badve, S., Saxena, R., Henegariu, O., Sell, S., Crawford, J. M. & Krause, D. S.: "Derivation of hepatocytes from bone marrow cells in mice after radiation-induced myeloablation" (2000) *Hepatology* 31, 235-40.

Thomson, J. A., Itskovitz-Eldor, J., Shapiro, S. S., Waknitz, M. A., Swiergiel, J. J., Marshall, V. S., and Jones, J. M.: "ES cell lines derived from human blastocysts". (1998) *Science* 282:114-7.

Thomson, J., Kalisman J., Golos, J., Durning, M., Harris, C., Becker, R., Hearn, J.: "Isolation of a primate embryonic stem cell line". (1995) *Proc. Natl. Acad. Sci. U.S.A.* 92: 7844-8.

Tsai, R. Y. and McKay, R. D.: "Cell contact regulates fate choice by cortical stem cells". (2000) *J. Neurosci.* 20:3725-35.

Tsukamoto, et al., U.S. Pat. No. 5,750,397

Tsukamoto, et al., U.S. Pat. No. 5,716,827

Xu et al. (2001) Feeder-free growth of undifferentiated human embryonic stem cells, Nature Biotechnology, 19:971.

Vescovi, A., Reynolds, B., Fraser, D. & Weiss, S.: "bFGF regulates the proliferative fate of unipotent (neuronal) and bipotent (neuronal/astroglial) EGF-generated CNS progenitor cells" (1993) *Neuron* 11, 951-66.

Vescovi, A. L., Paraati, E. A., Gritti, A., Poulin, P., Ferrario, M., Wanke, E., Frolichsthal-Schoeller, P., Cova, L., Arcellana-Panlilio, M., Colombo, A., and Galli, R.: "Isolation and cloning of multipotential stem cells from the embryonic human CNS and establishment of transplantable human NSC lines by epigenetic stimulation". (1999) *Exp Neurol* 156:71-83.

Wagner, J., Akerud, P., Castro, D. S., Holm, P. C., Canals, J. M., Snyder, E. Y., Perlmann, T. & Arenas, E.: "Induction of a midbrain dopaminergic phenotype in Nurr1-overexpressing NSCs by type 1 astrocytes" (1999) *Nat Biotech* 17, 653-9.

Wang, S., Wu, H., Jiang, J., Delohery, T. M., Isdell, F. & Goldman, S. A.: "Isolation of neuronal precursors by sorting embryonic forebrain transfected with GFP regulated by the T alpha 1 tubulin promoter" (1998) *Nat Biotechnol* 16, 196-201.

Wang, S., Roy, N. S., Benraiss, A. & Goldman, S. A.: "Promoter-based isolation and fluorescence-activated sorting of mitotic neuronal progenitor cells from the adult mammalian ependymal/subependymal zone" (2000) *Dev Neurosci.* 22, 167-76.

Watt, F.: "Epidermal stem cells: markers patterning and the control of stem cell fate". (1997) *Philos Trans R Soc Lond B Biol Sci* 353: 831-6.

Weissman, I. L.: "Translating stem and progenitor cell biology to the clinic: barriers and opportunities". (2000) *Science* 287:1442-6.

Whittemore, S. R., Morassutti, D. J., Walters, W. M., Liu, R. H. & Magnuson, D. S.: "Mitogen and substrate differentially affect the lineage restriction of adult rat subventricular zone neural precursor cell populations" (1999) *Exp Cell Res* 252, 75-95.

Williams, R. L., Hilton, D. J., Pease, S., Willson, T. A., Stewart, C. If, Gearing, D. P., Wagner, E. F., Metcalf, D., Nicola, N. A., and Gough, N. M.: "Myeloid leukemia inhibitory factor maintains the developmental potential of ES cells". (1988) *Nature* 336: 684-7.

Wood, H. B. and Episkopou, V.: "Comparative expression of the mouse Sox1, Sox2 and Sox3 genes from pre-gastrulation to early somite stages" (1999) *Mech Dev.* 86(1-2): 197-201.

Woodbury, D., Schwarz, E. J., Prockop, D. J., and Black, I. B.: "Adult rat and human bone marrow stromal cells differentiate into neurons". (2000) *J Neurosci Res* 15:364-70.

Ying, Q. Y., Nichols, J., Evans, E. P. & Smith, A. G.: "Changing potency by spontaneous fusion" (2002) *Nature* 416, 545-8.

Yoo, J. U., Barthel, T. S., Nishimura, K., Solchaga, L., Caplan, A. I., Goldberg, V. M., Johnstone, B.: "Then chondrogenic potential of human bone-marrow-derived mesenchymal progenitor cells". (1998) *J Bone Joint Surg Am.* 12:1745-57.

Young, H., et al., U.S. Pat. No. 5,827,735.

Yoshiura, K.; Leysens, N. J.; Chang, J.; Ward, D.; Murray, J. C.; Muenke, M.: Genomic structure, sequence, and mapping of human FGF8 with no evidence for its role in craniosynostosis/limb defect syndromes. Am. J. Med. Genet. 72: 354-362, 1997

---

We claim:

1. A method for inducing stem cells to differentiate into neuronal cells comprising:
   a) culturing said stem cells with basic fibroblast growth factor;
   b) culturing the cells of step a) with fibroblast growth factor 8 and Sonic Hedgehog;
   c) culturing the cells of step b) with brain-derived neurotrophic factor; and
   d) co-culturing the cells of step c) with astrocytes;
   wherein said cells are cultured according to steps 1) through d) for at least seven days at each step.

2. The method of claim 1, wherein the stem cells are mammalian stem cells.

3. The method of claim 1, wherein the stem cells are human stem cells.

4. A method for inducing cells to differentiate into neuronal cells comprising co-culturing the cells with astrocytes, said cells having gone through the steps of
   a) culturing stem cells with basic fibroblast growth factor;
   b) culturing the cells of step a) with fibroblast growth factor 8 and Sonic Hedgehog; and
   c) culturing the cells of step b) with brain-derived neurotrophic factor;
   wherein said cells are cultured according to steps a) through c) for at least seven days at each step.

* * * * *

UNITED STATES PATENT AND TRADEMARK OFFICE
CERTIFICATE OF CORRECTION

PATENT NO. : 8,426,200 B2
APPLICATION NO. : 10/561826
DATED : April 23, 2013
INVENTOR(S) : Catherine M. Verfaillie et al.

It is certified that error appears in the above-identified patent and that said Letters Patent is hereby corrected as shown below:

In the Specification

In column 1, lines 14-16, please delete the two (2) sentences

"This work was supported by NIH Grants RO1-DK061847, RO1-DK58295. The government may have certain rights to the invention."

and insert

--This invention was made with government support under R01-DK061847 and R01-DK058295 awarded by the National Institutes of Health. The government has certain rights in the invention.--

In the Claims

In Claim 1, column 47, line 55, please delete "steps 1)" and insert --steps a)--.

Signed and Sealed this
Twenty-third Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,426,200 B2  
APPLICATION NO. : 10/561826  
DATED            : April 23, 2013  
INVENTOR(S)      : Verfaillie et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 698 days.

Signed and Sealed this

Eighth Day of September, 2015

Michelle K. Lee
*Director of the United States Patent and Trademark Office*